(12) United States Patent
Palti-Wasserman et al.

(10) Patent No.: US 11,457,847 B2
(45) Date of Patent: Oct. 4, 2022

(54) LIE DETECTOR BASED ON MONITORING OF PUPIL DILATION

(71) Applicant: Eye-Minders Ltd., Haifa (IL)

(72) Inventors: Daphna Palti-Wasserman, Haifa (IL); Arik Lilling, Mazkeret Batya (IL); Ofek Wasserman, Haifa (IL); Neta Lerman, Haifa (IL); Benny Karov, Ramat Hasharon (IL); Maayan Wasserman, Haifa (IL)

(73) Assignee: Eye-Minders Ltd., Haifa (IL)

( * ) Notice: Subject to any disclaimer, the term of this patent is extended or adjusted under 35 U.S.C. 154(b) by 425 days.

(21) Appl. No.: 16/863,539

(22) Filed: Apr. 30, 2020

(65) Prior Publication Data

US 2021/0338124 A1    Nov. 4, 2021

(51) Int. Cl.
*G10L 15/22* (2006.01)
*A61B 5/16* (2006.01)
*A61B 3/11* (2006.01)

(52) U.S. Cl.
CPC .............. *A61B 5/164* (2013.01); *A61B 3/112* (2013.01); *A61B 5/163* (2017.08); *G10L 15/22* (2013.01)

(58) Field of Classification Search
CPC ......... A61B 5/164; A61B 5/163; A61B 3/112; G10L 15/22
See application file for complete search history.

(56) References Cited

U.S. PATENT DOCUMENTS

| 2008/0104415 A1 | 5/2008 | Palti-Wasserman et al. |
| 2009/0216092 A1 | 8/2009 | Waldorf et al. |
| 2011/0077546 A1 | 3/2011 | Fabian |
| 2011/0109879 A1 | 5/2011 | Palti-Wasserman et al. |
| 2013/0139259 A1 | 5/2013 | Tegreene |
| 2015/0294149 A1 | 10/2015 | Palti-Wasserman et al. |
| 2015/0355815 A1 | 12/2015 | Palti-Wasserman |
| 2020/0060598 A1 | 2/2020 | Palti-Wasserman |

FOREIGN PATENT DOCUMENTS

WO      2018207183 A1    11/2018

OTHER PUBLICATIONS

U.S. Appl. No. 16/863,545, filed Apr. 30, 2020, Palti-Wasserman et al, Unpublished co-pending application.
Harris, "An Eye-Scanning Lie Detector is Forging a Dystopian Future," Wired, Dec. 4, 2018.
Nurcin et al., "Lie detection on pupil size by back propagation neural network," Procedia Computer Science, vol. 120, pp. 417-421, 2017.

(Continued)

*Primary Examiner* — Mathew Franklin Gordon
(74) *Attorney, Agent, or Firm* — Potomac Law Group, PLLC

(57) ABSTRACT

Deception can be evaluated by presenting a set of sentences or words to a testee, including some sentences or words that are expected to evoke significant pupil dilation in a testee who is lying and other sentences or words that are not expected to evoke significant pupil dilation in the testee. Changes in the testee's pupil size are compared to ascertain whether a pupil-dilation response to certain sentences or words is larger than for other sentences or words, and an indication of deceptiveness or non-deceptiveness is output based on the results of the ascertaining.

29 Claims, 10 Drawing Sheets

(56) References Cited

OTHER PUBLICATIONS

Winn et al., "Best Practices and Advice for Using Pupillometry to Measure Listening Effort: An Introduction for Those Who Want to Get Started," Trends in Hearing, vol. 22, 233121658800869, Sep. 2018.

International Search Report and Written Opinion issued in application No. PCT/IB2021/053058 dated Jun. 18, 2021.

Wang, "Pupil Dilation and Eye-tracking," retrieved from the Internet: http://citeseerx.ist.psu.edu/viewdoc/download: jsessionid=C8BA23F8571802ADC4AA5478945FRF11?, Oct. 2009.

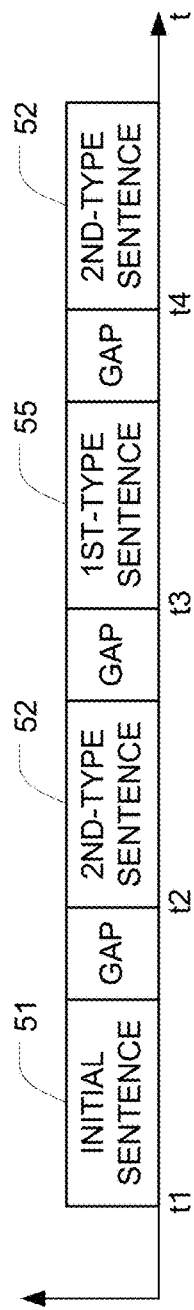
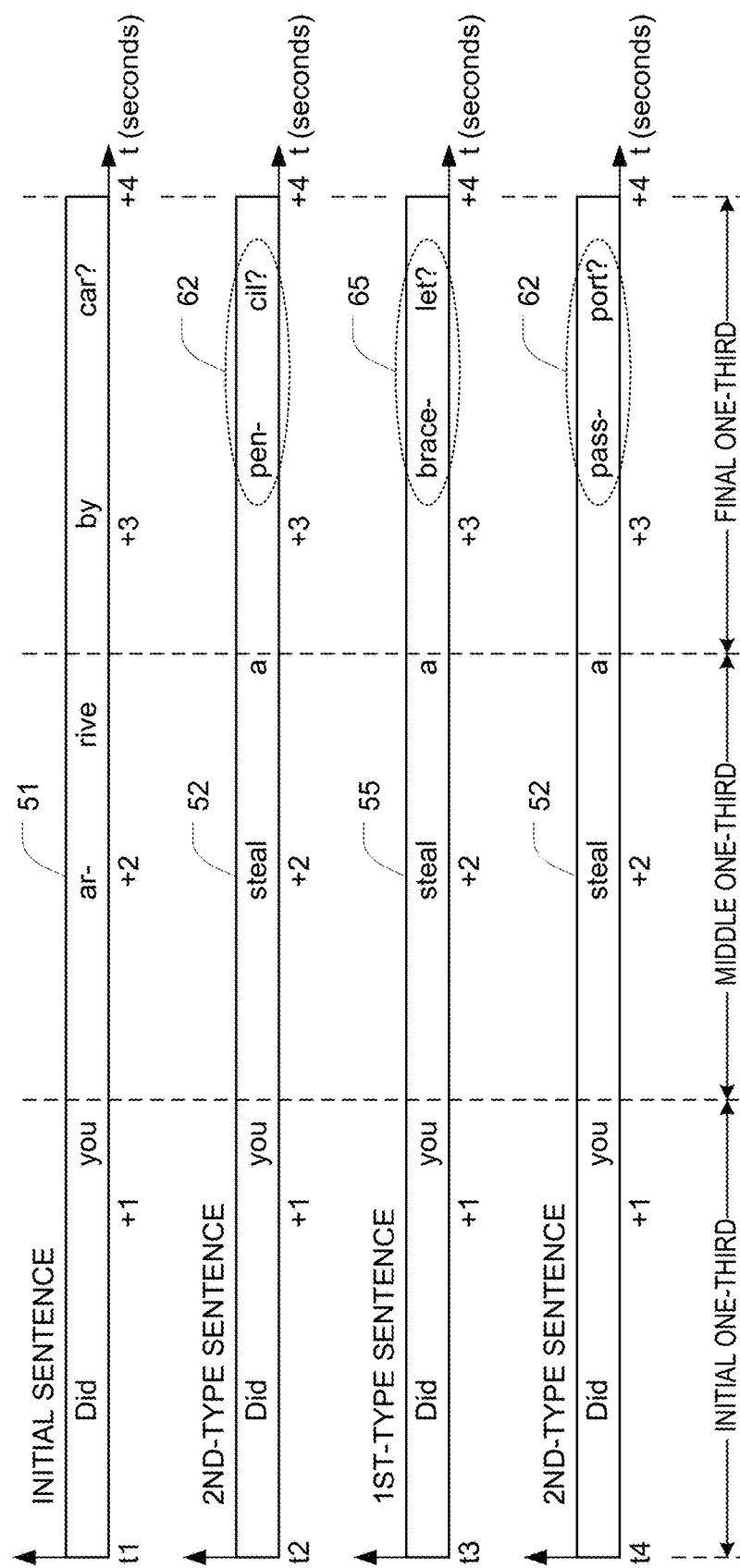
FIG. 3
FIG. 4

LIE DETECTOR BASED ON MONITORING OF PUPIL DILATION

BACKGROUND

Polygraphs, popularly referred to as lie detectors, measure physiological indicators of stress, which is an indicator of lying. When a person lies, they experience typical autonomic reactions, triggered by stress, that are not easily controlled by the conscious mind. These autonomic reactions may include an increase in skin conductivity, heart rate, respiration rate, blood pressure, capillary dilation, and muscular movement. The polygraph detects these autonomic reactions. It turns out, however, that these same autonomic reactions can result from other factors associated with and emotional states such as: fear, anger, familiarity, significance to the subject, and surprise. This decreases the capability of a polygraph to detect liars with high sensitivity and specificity. In addition, some people have found ways to cheat a polygraph system. Examples include taking sedatives to reduce anxiety, using an antiperspirant to prevent sweating, and positioning pins or biting parts of the mouth after each question to present a constant physiological response. Moreover, polygraphs are intrusive, require an expert examiner, can be fooled, and cannot be used for screening crowds or for working in the field because a single polygraph examination can take hours.

SUMMARY OF THE INVENTION

One aspect of the invention is directed to a first apparatus for evaluating whether a testee is being deceptive. The first apparatus comprises an image sensor configured to capture a plurality of sequential images of the testee's pupil; a processor configured to determine a size of the testee's pupil in the plurality of sequential images; a circuit that generates an audio output; and a controller. The controller is programmed to control the circuit so that the circuit outputs an audio signal corresponding to a set of sentences. The set of sentences includes an initial sentence, a first-type sentence, and a plurality of second-type sentences. The first-type sentence is expected to evoke significant pupil dilation in a testee who is being deceptive and not to evoke significant pupil dilation in a testee who is not being deceptive, and each of the second-type sentences is not expected to evoke significant pupil dilation in the testee. The initial sentence is output prior to the outputting of the first-type sentence and the plurality of second-type sentences. The controller is further programmed to monitor changes in the determined size of the testee's pupil during the outputting of the first-type sentence and the plurality of second-type sentences and during any responses to the first-type sentence and the plurality of second-type sentences made by the testee. The controller is further programmed to compare changes in the determined size of the testee's pupil in response to the first-type sentence with changes in the determined size of the testee's pupil in response to the second-type sentences to ascertain whether a pupil-dilation response to the first-type sentence is larger than a pupil-dilation response to each of the plurality of second-type sentences. The controller is further programmed to output an indication of deceptiveness or non-deceptiveness based on the ascertaining of whether the pupil-dilation response to the first-type sentence is larger than the pupil-dilation response to each of the plurality of second-type sentences. The first-type sentence and each of the second-type sentences are all in the same language. The average volume of each of the portions of the audio signal that corresponds to a second-type sentence is within 10 dB of the average volume of the portion of the audio signal that corresponds to the first-type sentence. The first-type sentence and each of the second-type sentences has a duration of less than 5 s. And gaps of at least 3 s are interposed between adjacent sentences within the set of sentences.

In some embodiments of the first apparatus, the controller is further programmed to (a) output an indication of deceptiveness when the controller ascertains that the pupil-dilation response to the first-type sentence is larger than the pupil-dilation response to each of the plurality of second-type sentences, and (b) output an indication of non-deceptiveness when the controller ascertains that the pupil-dilation response to the first-type sentence is not larger than the pupil-dilation response to each of the plurality of second-type sentences.

In some embodiments of the first apparatus, portions of the audio signal corresponding to the first-type sentence and the plurality of second-type sentences are output using the same voice, the entire set of sentences is output within 2 minutes, and the set of sentences that is output contains between 4 and 10 sentences.

In some embodiments of the first apparatus, the controller is further programmed to ascertain whether a pupil-dilation response to the first-type sentence is at least 10% larger than a pupil-dilation response to each of the plurality of second-type sentences.

Some embodiments of the first apparatus further comprise an audio amplifier and a speaker. In these embodiments, the audio amplifier receives the audio output from the circuit, and an output of the audio amplifier drives the speaker.

Some embodiments of the first apparatus further comprise a light source configured to control a level of illumination that arrives at the testee's pupil in response to instructions received from the controller. In these embodiments, the controller is further programmed to send the instructions to the light source.

In some embodiments of the first apparatus, a single integrated circuit serves as both the processor and the controller.

In some embodiments of the first apparatus, the set of sentences further includes a third-type sentence that is expected to evoke significant pupil dilation in a testee who is not being deceptive. In these embodiments the controller is further programmed to (a) compare changes in the testee's pupil size in response to the third-type sentence with changes in the testee's pupil size in response to the first-type sentence to ascertain whether a pupil-dilation response to the first-type sentence is larger than a pupil-dilation response to the third-type sentence, (b) output an indication of deceptiveness when the controller ascertains that the pupil-dilation response to the first-type sentence is larger than the pupil-dilation response to each of the plurality of second-type sentences and is also larger than the pupil-dilation response to the third-type sentence, and (c) output an indication of non-deceptiveness when the controller ascertains that the pupil-dilation response to the third-type sentence is larger than the pupil-dilation response to the first-type sentence or when the controller ascertains that the pupil-dilation response to the first-type sentence is not larger than the pupil-dilation response to each of the plurality of second-type sentences.

In some embodiments of the first apparatus, the grammatical structure, duration, level of complexity, and language style of each of the second-type sentences is similar to the grammatical structure, duration, level of complexity, and language style of the first-type sentence.

In some embodiments of the first apparatus, the first-type sentence includes a material keyword, each of the second-type sentences includes a respective other keyword, and the position of the respective other keyword within each of the second-type sentences is similar to the position of the material keyword within the first-type sentence. Any two given keywords are deemed to have a similar position within a respective sentence when the two given keywords are either (a) both positioned in the initial one-third of the respective sentence, (b) both positioned in the middle one-third of the respective sentence, or (c) both positioned in the last one-third of the respective sentence.

Another aspect of the invention is directed to a first method of evaluating whether a testee is being deceptive. The first method comprises presenting a set of sentences to the testee. The set of sentences includes an initial sentence, a first-type sentence, and a plurality of second-type sentences. The first-type sentence is expected to evoke significant pupil dilation in a testee who is being deceptive and not to evoke significant pupil dilation in a testee who is not being deceptive. Each of the second-type sentences is not expected to evoke significant pupil dilation in the testee. The initial sentence is presented to the testee prior to the presenting of the first-type sentence and the plurality of second-type sentences. The first method also comprises monitoring changes in the testee's pupil size during the presenting of the first-type sentence and the plurality of second-type sentences and during any responses to the first-type sentence and the plurality of second-type sentences made by the testee. The first method also comprises comparing changes in the testee's pupil size in response to the first-type sentence with changes in the testee's pupil size in response to the second-type sentences to ascertain whether a pupil-dilation response to the first-type sentence is larger than a pupil-dilation response to each of the plurality of second-type sentences. And the first method also comprises outputting an indication of deceptiveness or non-deceptiveness based on the ascertaining of whether the pupil-dilation response to the first-type sentence is larger than the pupil-dilation response to each of the plurality of second-type sentences. In this first method, the first-type sentence and each of the second-type sentences are all in the same language, the average volume of each of the second-type sentences is within 10 dB of the average volume of the first-type sentence, the first-type sentence and each of the second-type sentences has a duration of less than 5 s, and gaps of at least 3 s are interposed between adjacent sentences within the set of sentences.

In some instances of the first method, the outputting comprises (a) outputting an indication of deceptiveness when the comparing reveals that the pupil-dilation response to the first-type sentence is larger than the pupil-dilation response to each of the plurality of second-type sentences, and (b) outputting an indication of non-deceptiveness when the comparing reveals that the pupil-dilation response to the first-type sentence is not larger than the pupil-dilation response to each of the plurality of second-type sentences.

In some instances of the first method, the first-type sentence and the plurality of second-type sentences are all in the same voice, the entire set of sentences is presented to the testee within 2 minutes, and the set of sentences that is presented to the testee contains between 4 and 10 sentences.

Some instances of the first method further comprise controlling a level of illumination that arrives at the testee's pupil.

In some instances of the first method, the set of sentences further includes a third-type sentence that is expected to evoke significant pupil dilation in a testee who is not being deceptive. In these instances, the method further comprises (a) comparing changes in the testee's pupil size in response to the third-type sentence with changes in the testee's pupil size in response to the first-type sentence to ascertain whether a pupil-dilation response to the first-type sentence is larger than a pupil-dilation response to the third-type sentence, (b) outputting an indication of deceptiveness when a pupil-dilation response to the first-type sentence is larger than the pupil-dilation response to each of the plurality of second-type sentences and is also larger than the pupil-dilation response to the third-type sentence, and (c) outputting an indication of non-deceptiveness when the pupil-dilation response to the third-type sentence is larger than the pupil-dilation response to the first-type sentence or when the pupil-dilation response to the first-type sentence is not larger than the pupil-dilation response to each of the plurality of second-type sentences.

In some instances of the first method, the grammatical structure, duration, level of complexity, and language style of each of the second-type sentences is similar to the grammatical structure, duration, level of complexity, and language style of the first-type sentence.

In some instances of the first method, the first-type sentence includes a material keyword, and each of the second-type sentences includes a respective other keyword. The position of the respective other keyword within each of the second-type sentences is similar to the position of the material keyword within the first-type sentence. Any two given keywords are deemed to have a similar position within a respective sentence when the two given keywords are either (a) both positioned in the initial one-third of the respective sentence, (b) both positioned in the middle one-third of the respective sentence, or (c) both positioned in the last one-third of the respective sentence.

Another aspect of the invention is directed to a second apparatus for evaluating whether a testee is being deceptive. The second apparatus comprises an image sensor configured to capture a plurality of sequential images of the testee's pupil; a processor configured to determine a size of the testee's pupil in the plurality of sequential images; a circuit that generates an audio output; and a controller. The controller is programmed to control the circuit so that the circuit outputs an audio signal corresponding to (a) an introductory phrase or sentence and (b) a set of words. The set of words is output after the introductory phrase or sentence, with gaps of at least 2 s interposed between words within the set. The set of words includes an initial word, a first-type word, and a plurality of second-type words. The first-type word is expected to evoke significant pupil dilation in a testee who is being deceptive and not to evoke significant pupil dilation in a testee who is not being deceptive. Each of the second-type words is not expected to evoke significant pupil dilation in the testee. The initial word is presented to the testee prior to the presenting of the first-type word and the plurality of second-type words. The entire set of words is presented to the testee in less than 2 minutes, and the set of words contains less than 20 words. The controller is further programmed to monitor changes in the testee's pupil size during the presenting of the first-type word and the plurality of second-type words and during any responses to the first-type word and the plurality of second-type words made by the testee. The controller is further programmed to compare changes in the testee's pupil size in response to the first-type word with changes in the testee's pupil size in response to the second-type words to ascertain whether a pupil-dilation response to the first-type word is larger than a pupil-dilation response to each of the plurality of second-type words. And the controller is further programmed to output an indication of deceptiveness or non-deceptiveness based on the ascertaining of whether the pupil-dilation response to the first-type word is larger than the pupil-dilation response to each of the plurality of second-type words. In these embodiments, the first-type word and each of the second-type words are all in the same language, and the first-type word and each of the second-type words all have volumes within 10 dB of each other.

In some embodiments of the second apparatus, the controller is further programmed to (a) output an indication of deceptiveness when the controller ascertains that the pupil-dilation response to the first-type word is larger than the pupil-dilation response to each of the plurality of second-type words, and (b) output an indication of non-deceptiveness when the controller ascertains that the pupil-dilation response to the first-type word is not larger than the pupil-dilation response to each of the plurality of second-type words.

In some embodiments of the second apparatus, the controller is further programmed to control a level of illumination that arrives at the testee's pupil.

In some embodiments of the second apparatus, the set of words further includes a third-type word that is expected to evoke significant pupil dilation in a testee who is not being deceptive. In these embodiments, the controller is further programmed to (a) compare changes in the testee's pupil size in response to the third-type word with changes in the testee's pupil size in response to the first-type word to ascertain whether a pupil-dilation response to the first-type word is larger than a pupil-dilation response to the third-type word, (b) output an indication of deceptiveness when the controller ascertains that the pupil-dilation response to the first-type word is larger than the pupil-dilation response to each of the plurality of second-type words and is also larger than the pupil-dilation response to the third-type word, and (c) output an indication of non-deceptiveness when the controller ascertains that the pupil-dilation response to the third-type word is larger than the pupil-dilation response to the first-type word or when the controller ascertains that the pupil-dilation response to the first-type word is not larger than the pupil-dilation response to each of the plurality of second-type words.

In some embodiments of the second apparatus, the first-type word and each of the second-type words are presented in the same voice. Optionally, in these embodiments, the first-type word and each of the second-type words have a similar level of complexity and a similar language style.

Another aspect of the invention is directed to a second method of evaluating whether a testee is being deceptive. The second method comprises presenting an introductory phrase or sentence to the testee. The second method also comprises presenting a set of words to the testee after the introductory phrase or sentence has been presented to the testee, with gaps of at least 2 s interposed between words within the set. The set of words includes an initial word, a first-type word, and a plurality of second-type words. The first-type word is expected to evoke significant pupil dilation in a testee who is being deceptive and not to evoke significant pupil dilation in a testee who is not being deceptive. Each of the second-type words is not expected to evoke significant pupil dilation in the testee. The initial word is presented to the testee prior to the presenting of the first-type word and the plurality of second-type words, the entire set of words is presented to the testee in less than 2 minutes, and the set of words contains less than 20 words. The second method also comprises monitoring changes in the testee's pupil size during the presenting of the first-type word and the plurality of second-type words and during any responses to the first-type word and the plurality of second-type words made by the testee. The second method also comprises comparing changes in the testee's pupil size in response to the first-type word with changes in the testee's pupil size in response to the second-type words to ascertain whether a pupil-dilation response to the first-type word is larger than a pupil-dilation response to each of the plurality of second-type words. The second method also comprises outputting an indication of deceptiveness or non-deceptiveness based on the ascertaining of whether the pupil-dilation response to the first-type word is larger than the pupil-dilation response to each of the plurality of second-type words. In the second method, the first-type word and each of the second-type words are all in the same language, and the first-type word and each of the second-type words all have volumes within 10 dB of each other.

In some instances of the second method, the outputting comprises (a) outputting an indication of deceptiveness when the comparing reveals that the pupil-dilation response to the first-type word is larger than the pupil-dilation response to each of the plurality of second-type words, and (b) outputting an indication of non-deceptiveness when the comparing reveals that the pupil-dilation response to the first-type word is not larger than the pupil-dilation response to each of the plurality of second-type words.

Some instances of the second method further comprise controlling a level of illumination that arrives at the testee's pupil.

In some instances of the second method, the set of words further includes a third-type word that is expected to evoke significant pupil dilation in a testee who is not being deceptive. In these instances, the second method further comprises (a) comparing changes in the testee's pupil size in response to the third-type word with changes in the testee's pupil size in response to the first-type word to ascertain whether a pupil-dilation response to the first-type word is larger than a pupil-dilation response to the third-type word, (b) outputting an indication of deceptiveness when the pupil-dilation response to the first-type word is larger than the pupil-dilation response to each of the plurality of second-type words and is also larger than the pupil-dilation response to the third-type word, and (c) outputting an indication of non-deceptiveness when the pupil-dilation response to the third-type word is larger than the pupil-dilation response to the first-type word or when the pupil-dilation response to the first-type word is not larger than the pupil-dilation response to each of the plurality of second-type words.

In some instances of the second method, the first-type word and each of the second-type words are presented in the same voice. Optionally, in these instances, the first-type word and each of the second-type words have a similar level of complexity and a similar language style.

Another aspect of the invention is directed to a third apparatus for evaluating whether a testee is being deceptive. The third apparatus comprises an image sensor configured to capture a plurality of sequential images of the testee's pupil; a processor configured to determine a size of the testee's pupil in the plurality of sequential images; a circuit that generates an audio output; and a controller. The controller is programmed to control the circuit so that the circuit outputs an audio signal corresponding to a set of sentences. The set of sentences includes an initial sentence and at least three first-type sentences. Each of the first-type sentences is expected to evoke significant pupil dilation in a testee who is being deceptive and not to evoke significant pupil dilation in a testee who is not being deceptive. The initial sentence is output prior to the outputting of the first-type sentences. The controller is further programmed to monitor changes in the determined size of the testee's pupil during the outputting of the first-type sentences and during any responses to the first-type sentences made by the testee. The controller is further programmed to compare changes in the determined size of the testee's pupil in response to each of the first-type sentences to ascertain whether a pupil-dilation response to each respective one of the first-type sentences is at least 10% larger than a pupil-dilation response to at least two of the other first-type sentences. And the controller is further programmed to output an indication of deceptiveness or non-deceptiveness for at least one of the first-type sentences based on a result of the ascertaining. In the third apparatus, the first-type sentences are all in the same language, the average volume of each of the portions of the audio signal that corresponds to each of the first-type sentences are all within 10 dB of each other, each of the first-type sentences has a duration of less than 5 s, and gaps of at least 3 s are interposed between adjacent sentences within the set of sentences.

In some embodiments of the third apparatus, the controller is further programmed to (a) output an indication of deceptiveness for a respective one of the first-type sentences when the controller ascertains that the pupil-dilation response to the respective first-type sentence is at least 10% larger than a pupil-dilation response to at least two of the other first-type sentences, and (b) output an indication of non-deceptiveness when the controller ascertains that no pupil-dilation response to any given one of the first-type sentences is at least 10% larger than a pupil-dilation response to at least two of the other first-type sentences.

In some embodiments of the third apparatus, portions of the audio signal corresponding to the first-type sentences are output using the same voice, the entire set of sentences is output within 2 minutes, and the set of sentences that is output contains between 4 and 10 sentences.

In some embodiments of the third apparatus, the controller is further programmed to ascertain whether a pupil-dilation response to any given one of the first-type sentences is at least 20% larger than a pupil-dilation response to at least two of the other first-type sentences.

Some embodiments of the third apparatus further comprise an audio amplifier and a speaker. The audio amplifier receives the audio output from the circuit, and an output of the audio amplifier drives the speaker.

Some embodiments of the third apparatus further comprise a light source configured to control a level of illumination that arrives at the testee's pupil in response to instructions received from the controller. In these embodiments, the controller is further programmed to send the instructions to the light source.

In some embodiments of the third apparatus, a single integrated circuit serves as both the processor and the controller.

In some embodiments of the third apparatus, the set of sentences further includes a third-type sentence that is expected to evoke significant pupil dilation in a testee who is not being deceptive. In these embodiments, the controller is further programmed to (a) compare changes in the testee's pupil size in response to the third-type sentence with changes in the testee's pupil size in response to each of the first-type sentences, (b) output an indication of deceptiveness for a respective one of the first-type sentences when the controller ascertains that the pupil-dilation response to the respective first-type sentence is at least 10% larger than the pupil-dilation response to at least two of the other first-type sentences and is also larger than the pupil-dilation response to the third-type sentence, and (c) output an indication of non-deceptiveness when the controller ascertains that the pupil-dilation response to each of the first-type sentences is smaller than the pupil-dilation response to the third-type sentence or when the controller ascertains that the pupil-dilation response to none of the first-type sentences is at least 10% larger than the pupil-dilation response to at least two other first-type sentences.

In some embodiments of the third apparatus, the grammatical structure, duration, level of complexity, and language style of all the first-type sentences are similar.

In some embodiments of the third apparatus, each of the first-type sentences includes a respective keyword, and the position of the respective keyword within each of the first-type sentences is similar. Any two given keywords are deemed to have a similar position within a respective sentence when the two given keywords are either (a) both positioned in the initial one-third of the respective sentence, (b) both positioned in the middle one-third of the respective sentence, or (c) both positioned in the last one-third of the respective sentence.

Another aspect of the invention is directed to a third method of evaluating whether a testee is being deceptive. The third method comprises presenting a set of sentences to the testee. The set of sentences includes an initial sentence and at least three first-type sentences. Each of the first-type sentences is expected to evoke significant pupil dilation in a testee who is being deceptive and not to evoke significant pupil dilation in a testee who is not being deceptive. The initial sentence is presented to the testee prior to the presenting of the first-type sentences. The third method also comprises monitoring changes in the testee's pupil size during the presenting of the first-type sentences and during any responses to the first-type sentences made by the testee. The third method also comprises comparing changes in the testee's pupil size in response to each of the first-type sentences to ascertain whether a pupil-dilation response to each respective one of the first-type sentences is at least 10% larger than a pupil-dilation response to at least two of the other first-type sentences. The third method also comprises outputting an indication of deceptiveness or non-deceptiveness for at least one of the first-type sentences based on a result of the ascertaining. The first-type sentences are all in the same language, the average volume of each of the first-type sentences is within 10 dB of each other, each of the first-type sentences has a duration of less than 5 s, and gaps of at least 3 s are interposed between adjacent sentences within the set of sentences.

In some instances of the third method, the outputting comprises (a) outputting an indication of deceptiveness for a respective one of the first-type sentences when the comparing reveals that the pupil-dilation response to the respective first-type sentence is at least 10% larger than a pupil-dilation response to at least two of the other first-type sentences, and (b) outputting an indication of non-deceptiveness when the comparing reveals that no pupil-dilation response to any given one of the first-type sentences is at least 10% larger than a pupil-dilation response to at least two of the other first-type sentences.

In some instances of the third method, the first-type sentences are all in the same voice, the entire set of sentences is presented to the testee within 2 minutes, and the set of sentences that is presented to the testee contains between 4 and 10 sentences.

Some instances of the third method further comprise controlling a level of illumination that arrives at the testee's pupil.

In some instances of the third method, the set of sentences further includes a third-type sentence that is expected to evoke significant pupil dilation in a testee who is not being deceptive. In these instances, the third method further comprises (a) comparing changes in the testee's pupil size in response to the third-type sentence with changes in the testee's pupil size in response to each of the first-type sentences, (b) outputting an indication of deceptiveness for a respective one of the first-type sentences when a pupil-dilation response to the respective first-type sentences is at least 10% larger than the pupil-dilation response to at least two of the other first-type sentences and is also larger than the pupil-dilation response to the third-type sentence, and (c) outputting an indication of non-deceptiveness when the pupil-dilation response to each of the first-type sentences is smaller than the pupil-dilation response to the third-type sentence or when the pupil-dilation response to none of the first-type sentences is at least 10% larger than the pupil-dilation response to at least two other first-type sentences.

In some instances of the third method, the grammatical structure, duration, level of complexity, and language style of all the first-type sentences are similar.

In some instances of the third method, each of the first-type sentences includes a respective keyword, and the position of the respective keyword within each of the first-type sentences is similar. Any two given keywords are deemed to have a similar position within a respective sentence when the two given keywords are either (a) both positioned in the initial one-third of the respective sentence, (b) both positioned in the middle one-third of the respective sentence, or (c) both positioned in the last one-third of the respective sentence.

Another aspect of the invention is directed to a fourth apparatus for evaluating whether a testee is being deceptive. The fourth apparatus comprises an image sensor configured to capture a plurality of sequential images of the testee's pupil; a processor configured to determine a size of the testee's pupil in the plurality of sequential images; a circuit that generates an audio output; and a controller. The controller is programmed to control the circuit so that the circuit outputs an audio signal corresponding to (a) an introductory phrase or sentence and (b) a set of words. The set of words is output after the introductory phrase or sentence, with gaps of at least 2 s interposed between words within the set. The set of words includes an initial word and at least three first-type words. Each of the first-type words is expected to evoke significant pupil dilation in a testee who is being deceptive and not to evoke significant pupil dilation in a testee who is not being deceptive. The initial word is presented to the testee prior to the presenting of the first-type words, the entire set of words is presented to the testee in less than 2 minutes, and the set of words contains less than 20 words. The controller is further programmed to monitor changes in the testee's pupil size during the presenting of the first-type words and during any responses to the first-type words made by the testee. The controller is further programmed to compare changes in the testee's pupil size in response to each of the first-type words to ascertain whether a pupil-dilation response to each respective one of the first-type words is at least 10% larger than a pupil-dilation response to at least two of the other first-type words. And the controller is further programmed to output an indication of deceptiveness or non-deceptiveness for at least one of the first-type words based on a result of the ascertaining. The first-type words are all in the same language, and the first-type words all have volumes within 10 dB of each other.

In some embodiments of the fourth apparatus, the controller is further programmed to (a) output an indication of deceptiveness for a respective one of the first-type words when the controller ascertains that the pupil-dilation response to the respective first-type word is at least 10% larger than a pupil-dilation response to at least two of the other first-type words, and (b) output an indication of non-deceptiveness when the controller ascertains that no pupil-dilation response to any given one of the first-type words is at least 10% larger than a pupil-dilation response to at least two of the other first-type words.

In some embodiments of the fourth apparatus, the controller is further programmed to control a level of illumination that arrives at the testee's pupil.

In some embodiments of the fourth apparatus, the set of words further includes a third-type word that is expected to evoke significant pupil dilation in a testee who is not being deceptive. In these embodiments, the controller is further programmed to (a) compare changes in the testee's pupil size in response to the third-type word with changes in the testee's pupil size in response to each of the first-type words, (b) output an indication of deceptiveness for a respective one of the first-type words when the controller ascertains that the pupil-dilation response to the respective first-type word is at least 10% larger than the pupil-dilation response to at least two of the other first-type words and is also larger than the pupil-dilation response to the third-type word, and (c) output an indication of non-deceptiveness when the controller ascertains that the pupil-dilation response to each of the first-type words is smaller than the pupil-dilation response to the third-type word or when the controller ascertains that the pupil-dilation response to none of the first-type words is at least 10% larger than the pupil-dilation response to at least two other first-type words.

In some embodiments of the fourth apparatus, all the first-type words are presented in the same voice. Optionally, in these embodiments, all the first-type words have a similar level of complexity and a similar language style.

Another aspect of the invention is directed to a fourth method of evaluating whether a testee is being deceptive. The fourth method comprises presenting an introductory phrase or sentence to the testee. The fourth method also comprises presenting a set of words to the testee after the introductory phrase or sentence has been presented to the testee, with gaps of at least 2 s interposed between words within the set. The set of words includes an initial word and at least three first-type words. Each of the first-type words is expected to evoke significant pupil dilation in a testee who is being deceptive and not to evoke significant pupil dilation in a testee who is not being deceptive. The initial word is presented to the testee prior to the presenting of the first-type words, the entire set of words is presented to the testee in less than 2 minutes, and the set of words contains less than 20 words. The fourth method also comprises monitoring changes in the testee's pupil size during the presenting of the first-type words and during any responses to the first-type words made by the testee. The fourth method also comprises comparing changes in the testee's pupil size in response to each of the first-type words to ascertain whether a pupil-dilation response to each respective one of the first-type words is at least 10% larger than a pupil-dilation response to at least two of the other first-type words. The fourth method also comprises outputting an indication of deceptiveness or non-deceptiveness for at least one of the first-type words based on a result of the ascertaining. The first-type words are all in the same language, and the first-type words all have volumes within 10 dB of each other.

In some instances of the fourth method, the outputting comprises (a) outputting an indication of deceptiveness for a respective one of the first-type words when the comparing reveals that the pupil-dilation response to the respective first-type word is at least 10% larger than a pupil-dilation response to at least two of the other first-type words, and (b) outputting an indication of non-deceptiveness when the comparing reveals that no pupil-dilation response to any given one of the first-type words is at least 10% larger than a pupil-dilation response to at least two of the other first-type words.

Some instances of the fourth method further comprise controlling a level of illumination that arrives at the testee's pupil.

In some instances of the fourth method, the set of words further includes a third-type word that is expected to evoke significant pupil dilation in a testee who is not being deceptive. In these instances, the method further comprises (a) comparing changes in the testee's pupil size in response to the third-type word with changes in the testee's pupil size in response to each of the first-type words, (b) outputting an indication of deceptiveness for a respective one of the first-type words when the pupil-dilation response to the respective first-type word is at least 10% larger than the pupil-dilation response to at least two of the other first-type words and is also larger than the pupil-dilation response to the third-type word, and (c) outputting an indication of non-deceptiveness when the pupil-dilation response to each of the first-type words is smaller than the pupil-dilation response to the third-type word or when the pupil-dilation response to none of the first-type words is at least 10% larger than the pupil-dilation response to at least two other first-type words.

In some instances of the fourth method, all the first-type words are presented in the same voice. Optionally, in these instances, all the first-type words have a similar level of complexity and a similar language style.

BRIEF DESCRIPTION OF THE DRAWINGS

FIG. 3 depicts an exemplary time sequence for presenting the set of sentences to the testee.

FIG. 4 depicts an example of presenting a set of sentences to a testee, where each of the sentences includes a respective keyword.

Various embodiments are described in detail below with reference to the accompanying drawings, wherein like reference numerals represent like elements.

DESCRIPTION OF THE PREFERRED EMBODIMENTS

Figure 1:
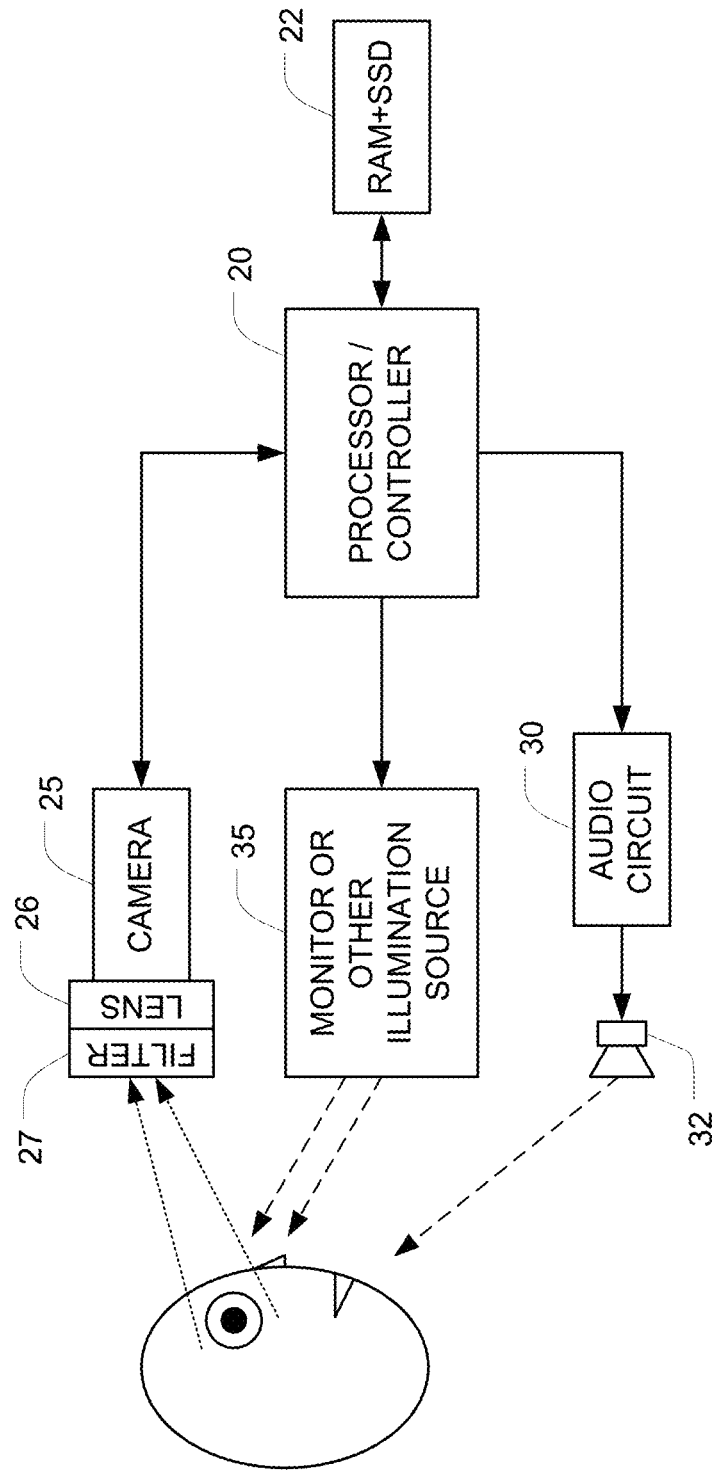
FIG. 1 is a block diagram of a system for evaluating whether a testee is being deceptive.

FIG. 1 is a block diagram of a system for evaluating whether a testee is being deceptive (e.g., whether the testee is lying or telling the truth). Operation of the system is controlled by a processor/controller 20. The processor/controller 20 performs both image processing operations and control operations, both of which are described below. The processor/controller 20 has access to a sufficient amount of RAM/SSD 21 (e.g., 16 GB of RAM and 512 GB of solid state disk space). In some embodiments, the processor/controller 20 is implemented using a single integrated circuit (e.g., an Intel Core i7 processor). But in alternative embodiments, the processor and control functions may be divided among two or more integrated circuits.

The system outputs audio signals to the testee via an audio circuit 30 (which optionally includes an audio frequency amplifier) that drives a speaker 32 or an alternative transducer (e.g. headphones), and the audio signals that the testee hears will depend on the signals that the processor/controller 20 sends to the audio circuit 30. As described below, the audio signals that are provided to the testee may be in the form of a set of sentences (e.g. questions, statements) or set of words. The processor/controller 20 is programmed to control the audio circuit 30 so that the audio circuit 30 outputs an audio signal corresponding to the set of sentences or the set of words. In some embodiments, this may be accomplished by pre-recording the set of sentences or the set of words and subsequently outputting the prerecorded sentences or words. In other embodiments, this may be accomplished by executing appropriate text-to-speech code.

A person's pupil-dilation responses may depend on a variety of factors including but not limited to the person's cognitive state, cognitive load, neuropsychological status, neurophysiological status, eye anatomy, illness, injury, intoxication, current state of mind, emotions (e.g., stress, fatigue, excitement, fear, surprise, anger, familiarity/affection) and personal characteristics. The embodiments described herein operate by evoking pupil-dilation responses from the testee (the source of the testee's pupil-dilation responses may be, for example, cognitive and/or emotional), analyzing those pupil-dilation responses, and deciding if the testee is being deceptive based on the analysis.

The system evaluates whether a testee is being deceptive by monitoring changes in the size of the testee's pupil. This is accomplished using an image sensor that captures a sequence of image frames that include the testee's pupil. The image sensor may be implemented, for example, using a camera 25 with a lens 26 that is aimed at the testee's face. In some preferred embodiments, the camera 25 is a UI-3060CP from IDS Imaging Development Systems GmbH, and the lens 26 is an M3514-MP 35 mm lens from Computar. Optionally, a filter 27 may be positioned in front of the lens 26. In some preferred embodiments, the filter 27 is an LP830-25.4 from Midopt. In some embodiments, frame rates between 30 frames per second (fps) and 120 fps are used to capture the images that include the testee's pupil. The number of image frames that must be captured will depend on the frame rate. For example, when the frame rate is 30 fps, and image data is captured for one minute, 1800 image frames will be captured by the image sensor and forwarded to the processor/controller 20.

The image data captured by the image sensor is provided to the processor/controller 20. The processor/controller 20 executes image processing routines to locate the testee's pupil in each frame of image data. One example of a suitable approach that may be used to locate the testee's pupil is to analyze each image using a threshold to binarize the image, apply a connected component algorithm to find all objects in the image, and detect the pupil by selecting the object which is round and has the correct physical size. A variety of alternative approaches will be apparent to persons skilled in the relevant art. After locating the testee's pupil in each frame, the processor/controller 20 executes image processing routines to determine the size of the testee's pupil in each frame. One way to accomplish this is by counting the number of pixels that correspond to the testee's pupil in each frame.

Some suitable approaches for evaluating the testee's pupil dilation response are described in *Best Practices and Advice for Using Pupillometry to Measure Listening Effort: An Introduction for Those Who Want to Get Started*, Mathew B. WINN, et al., Trends Hear. 2018 January-December; 22: 2331216518800869 (Sep. 28, 2018), which is incorporated herein by reference in its entirety. Alternative approaches will be apparent to persons skilled in the relevant art.

In certain situations described below, it can be beneficial to increase the illumination that arrives at the testee's eyes. A monitor 35 or another illumination source (e.g., a floor lamp) may be provided for this purpose. For example, the level of illumination that arrives at the testee's pupil could be increased using a conventional computer monitor 35, and having the processor/controller 20 send appropriate signals to the monitor 35 to display a bright background. Alternatively, in embodiments that rely on a floor lamp (not shown) to provide illumination, the processor/controller 20 could send a signal to turn on a smart outlet into which the floor lamp is plugged.

Figure 2:
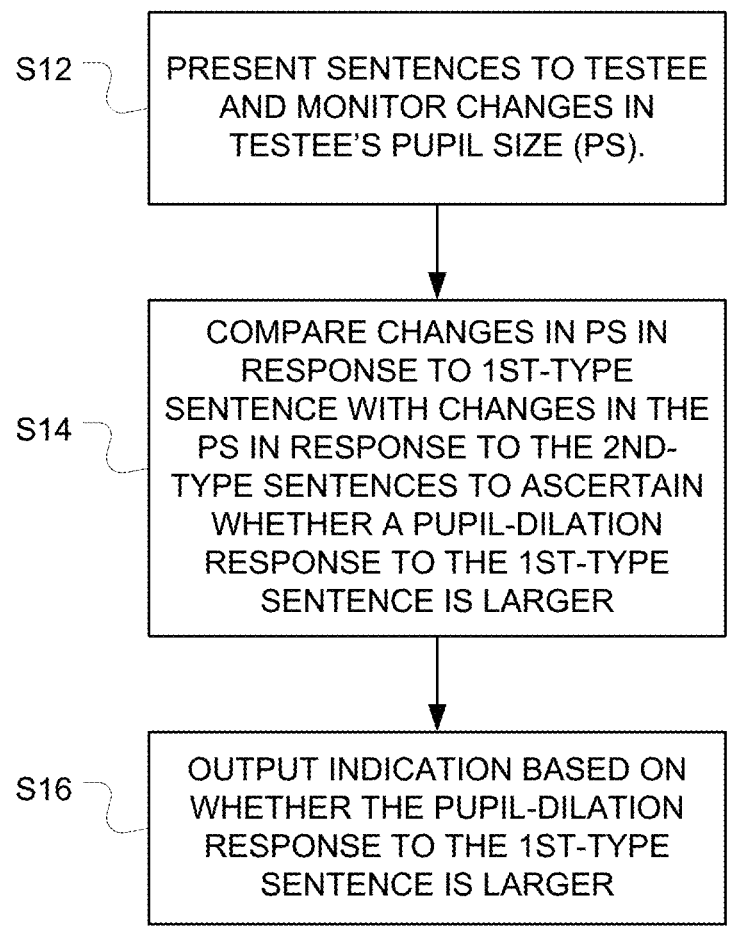
FIG. 2 is a flowchart for presenting a set of sentences to a testee, and evaluating deceptiveness by monitoring changes in size of the testee's pupil.

FIG. 2 depicts a flowchart for an embodiment in which a set of sentences is presented to the testee, and the system evaluates whether the testee is being deceptive by monitoring changes in the determined size of the testee's pupil. The steps S12-S16 of this flowchart are implemented by an appropriate program or programs running on the processor/controller 20 depicted in FIG. 1.

First, in step S12, the processor/controller 20 controls the audio circuit 30 so that the audio circuit outputs an audio signal corresponding to a set of sentences. The speaker 32 converts the audio signal to sounds that are presented to the testee. The set of sentences includes an initial sentence, a first-type sentence, and a plurality of second-type sentences. The sentences can be in the form of questions, statements, or any other form. In some embodiments, the first-type sentence and each of the plurality of second-type sentences are binary questions. As used herein, a "binary question" is a question that has only two possible answers (e.g., yes or no; true or false; etc.).

A "first-type sentence" is a sentence that the party administering the test cares about, and the evaluation of whether a testee is being deceptive applies to the first-type sentence. The "second-type sentence(s)" and optional "third-type sentence(s)" described below are presented to the testee so that the system has a baseline against which to compare the testee's response to the first-type sentence, with the ultimate goal of evaluating whether the testee is being deceptive with respect to the first-type sentence.

The first-type sentence is expected to evoke significant pupil dilation in a testee who is being deceptive and not to evoke significant pupil dilation in a testee who is not being deceptive. Each of the second-type sentences is not expected to evoke significant pupil dilation in the testee (although pupil dilation may, in fact, occur, depending on the content of the sentence for specific individuals).

Typically, a party that wants to detect deception is interested in a particular topic or a set of topics. Topics of interest could span a wide variety of subjects. Examples include (a) whether a person who is about to board an airplane is carrying explosives; (b) whether a particular person stole a particular item (e.g., a bracelet); and (c) whether a visitor to a prison is carrying contraband; etc.

The content of the first-type sentence is selected (before the testing begins) so that it relates to the specific topic in which the party administering the test is interested. Assume, for example, that the topic of interest is item (a) listed above. In this situation, the first-type sentence could be "do you have any explosives?" Presumably, any person carrying explosives onto an airplane would want to conceal that fact. As a result, asking that person "do you have any explosives?" will create a cognitive and/or emotional response in that person. And this cognitive and/or emotional response will give rise to an associated pupil-dilation response. On the other hand, asking the same question to an innocent person will not create a cognitive and/or emotional response and will therefore not evoke a significant pupil dilation in the innocent person. In another example, the question "did you steal a bracelet?" is expected to evoke significant pupil dilation in a testee who is being deceptive (i.e., in a testee who has stolen a bracelet), and not to evoke significant pupil dilation in testees who are not being deceptive (i.e., in testees who have not stolen a bracelet).

The content of the second-type sentences is selected so that it is not expected to evoke significant pupil dilation in the testee. Examples include pointed sentences of which the testee is not guilty such as "did you steal a passport?" (when the testee has not, in fact, stolen a passport). Other examples include innocuous questions like "do you have any shirts in your suitcase?" or "what's the weather like outside?". Preferably, care is taken in formulating the content of second-type sentences to minimize the following responses from the testee: memory processing; linguistic processing; recognition; computational processing; emotional responses (e.g., fear, stress, relaxation, happy, love); after thoughts; familiarity; interest/non-interest; surprise; embarrassment; confusion; amazement; laughter; anger; relief; a desire to comply. etc. Minimizing all of these responses from the testee will correspondingly minimize any impact on the testee's pupil-dilation response. Note that while the content of the second-type sentences is not expected to evoke significant pupil dilation, in certain situations the second-type sentences will, in fact, evoke a significant pupil dilation. This will depend on the content of the second-type sentence and the individual testee. But the pupil-dilation response induced by the second-type sentences is expected to be smaller than the pupil-dilation response induced by the first-type sentence for deceptive testees. Thus, the deceptive testee will be detected correctly even in these cases, and the non-deceptive testees will also be detected correctly.

One example where this FIG. 2 embodiment would be useful is in the context of a bar that wants to screen incoming people in a state where the minimum drinking age is 21. In this situation, the party administering the test (i.e., the bar) is only interested in whether the ID that is being presented by each person attempting to enter the bar is genuine or fake. For this situation, the first-type sentence would be "do you have a fake ID?"; and a suitable sequence of questions for this situation would be as follows: (1) Are you meeting a friend? (2) Do you have a fake ID? (3) Did you arrive by car? (4) did you bring a camera? In this example, question #1 is the initial sentence 51; question #2 is the first-type sentence 55; and questions #3 and 4 are the second-type sentences 52.

In some situations, the set of sentences may contain more than one first-type sentence. Assume, for example, that an airline wants to screen people who are about to board a plane. In this situation, the party administering the test needs to know whether each person is carrying any of the following items: guns, knives, explosives, and flammable liquids. For this situation, the following sequence of questions would be suitable: (1) Are you bringing any shirts on board? (2) Are you bringing any guns on board? (3) Are you bringing any food on board? (4) Are you bringing any knives on board? (5) Are you bringing any explosives on board? (6) Are you bringing a camera on board? (7) Are you bringing any flammable liquids on board? In this example, question #1 is the initial sentence 51; questions #2, 4, 5, and 7 are the first-type sentences 55; and questions #3 and 6 are the second-type sentences 52.

FIG. 3 depicts an example of a time sequence for presenting the set of sentences to the testee. More specifically, the initial sentence 51 is output prior to the first-type sentence 55 and the plurality of second-type sentences 52. But as between the first-type sentence and the second-type sentences 52, the sequence is not critical. Note that in the example depicted in FIG. 3, there is only a single first-type sentence 55 and only two second-type sentences 52. But in alternative examples, there could be more than one first-type sentence, and/or more than two second-type sentences.

Notably, the inventor has determined that the probability of success in evaluating whether a testee is being deceptive can be improved significantly by making the first-type sentence 55 and the second-type sentences 52 similar to each other in a number of important regards. More specifically, (1) the first-type sentence and each of the second-type sentences should all be in the same language (i.e., all of the sentences could be in English; or all of the sentences could be in French); (2) the average volume of each of the second-type sentences should be within 10 dB of the average volume of the first-type sentence; and (3) the first-type sentence and each of the second-type sentences should have a duration of less than 5 s.

Making the first-type sentence each of the second-type sentences similar to each other in these ways increases the probability that the pupil-dilation response observed by the system is attributable to the content of those sentences as opposed to other factors including but not limited to cognitive load, emotional load, etc. And this can advantageously increase the probability of success in evaluating whether a testee is being deceptive.

Optionally, the first-type sentence 55 and the second-type sentences 52 may be made similar to each other in additional ways, which can further improve the probability of success in evaluating whether a testee is being deceptive. In some embodiments, this is accomplished by making the grammatical structure and duration of each of the second-type sentences similar to the grammatical structure and duration of the first-type sentence; using similar tones for the first-type sentence and each of the second-type sentences; and/or outputting the first-type sentence and each of the second-type sentences in a similar voice. Optionally, the first-type sentence 55 in the second-type sentences 52 may be made similar to each other in the level of complexity and language style (e.g., modern American English vs. modern British English vs. Shakespearean English vs. New York slang). They may also be made similar to each other in duration, the number of words per sentence (e.g., less than 9 words per sentence). The peak volume of each of the second-type sentences may optionally also be set to be within 10 dB of the peak volume of the first-type sentence. Making the first-type sentence each of the second-type sentences similar to each other in one or more of these additional ways can further increases the probability that the pupil-dilation response observed by the system is attributable to the content of those sentences as opposed to other factors, which can further increase the probability of success in evaluating whether a testee is being deceptive.

In some embodiments, the first-type sentence 55 and the second-type sentences 52 are all true/false statements. In some embodiments, the first-type sentence 55 and the second-type sentences 52 are all binary questions.

FIG. 4 depicts yet another optional way to make the first-type sentence 55 and the second-type sentences 52 similar to each other. This is accomplished by incorporating a keyword into each of those sentences, and positioning all of the keywords at a similar location within each sentence. The keyword is the critical word in the sentence. In many cases, the keyword will be the object of the sentence. The first-type sentence 55 includes a material keyword 65, and each of the second-type sentences 52 includes a respective other keyword 62, and the position of the respective other keyword 62 within each of the second-type sentences 52 is similar to the position of the material keyword 65 within the first-type sentence 55.

FIG. 4 depicts an example of presenting a set of sentences 51-55 to a testee, where each of the sentences 52-55 includes a respective keyword 62-65. Assume, for example, that a bracelet has been stolen, and that the party administering the test suspects a particular person of stealing the bracelet. In this situation, "did you steal a bracelet?" would be the first-type sentence 55, and the other two options (i.e., "did you steal a pencil?" and "did you steal a passport?") would be the second-type sentences 52. Also, in this situation, the word "bracelet" would be the keyword 65 of the first-type sentence 55; and the words "pencil" and "passport" would be the keywords 62 of the second-type sentences 52.

To evaluate positional similarity, any two given keywords are deemed to have a similar position within a respective sentence when the two given keywords are either (a) both positioned in the initial one-third of the respective sentence, (b) both positioned in the middle one-third of the respective sentence, or (c) both positioned in the last one-third of the respective sentence. For example, in FIG. 4, the material keyword 65 ("bracelet") is positioned in the last one-third of the first-type sentence 55; and the two other keywords 62 ("pencil" and "passport") are also each positioned in the last one-third of the respective second-type sentence 52. All three of those keywords therefore have a similar position within their respective sentence. (The portions of each sentence that correspond to each one-third are demarcated by the labels on the bottom of FIG. 4 and the dashed vertical lines.) Maintaining consistency of the positions of the various keywords within the respective sentences provides a significant improvement in the probability of success in evaluating whether a testee is being deceptive. Making the first-type sentence each of the second-type sentences similar to each other in this additional way can further increases the probability that the pupil-dilation response observed by the system is attributable to the content of those sentences as opposed to other factors, which can further increase the probability of success in evaluating whether a testee is being deceptive.

Gaps are interposed between adjacent sentences 52, 55, as depicted in FIG. 3. Preferably, the gaps are at least 3 s long. In some embodiments, these gaps will all have the same duration. But in other embodiments, the size of the gaps may vary. In some embodiments the gap can also be calculated dynamically to improve performance. In these embodiments, the gap should be long enough to (a) make sure the previous response to the previous sentence is over and (b) make sure that the pupil is contracted enough for the system to detect dilation in response to a new sentence. Condition (b) may be determined by waiting until the pupil size is less than the median of the pupil size of a specific testee. The median can be calculated in a window including the previous pupil size during a question and response, or it can be calculated on the entire pupil response until the current time. Other estimations for a small enough pupil are possible. In addition, the shortest gap that fulfills these requirements may be selected, so the test will as short as possible.

In some embodiments, the entire set of sentences is preferably output in less than 2 minutes, and the set of sentences that is output preferably contains between 4-10 sentences.

Returning to FIG. 4, the first-type sentence 55 "did you steal a bracelet?" is expected to evoke significant pupil dilation in a testee who is being deceptive (i.e., in a testee who has stolen a bracelet), and not to evoke significant pupil dilation in a testee who is not being deceptive (i.e., in a testee who has not stolen a bracelet). Each of the second-type sentences 52 (i.e., "did you steal a pencil?" and "did you steal a passport?") is not expected to evoke significant pupil dilation in the testee (assuming we know in advance that the testee has not, in fact, stolen those items).

Figure 5:
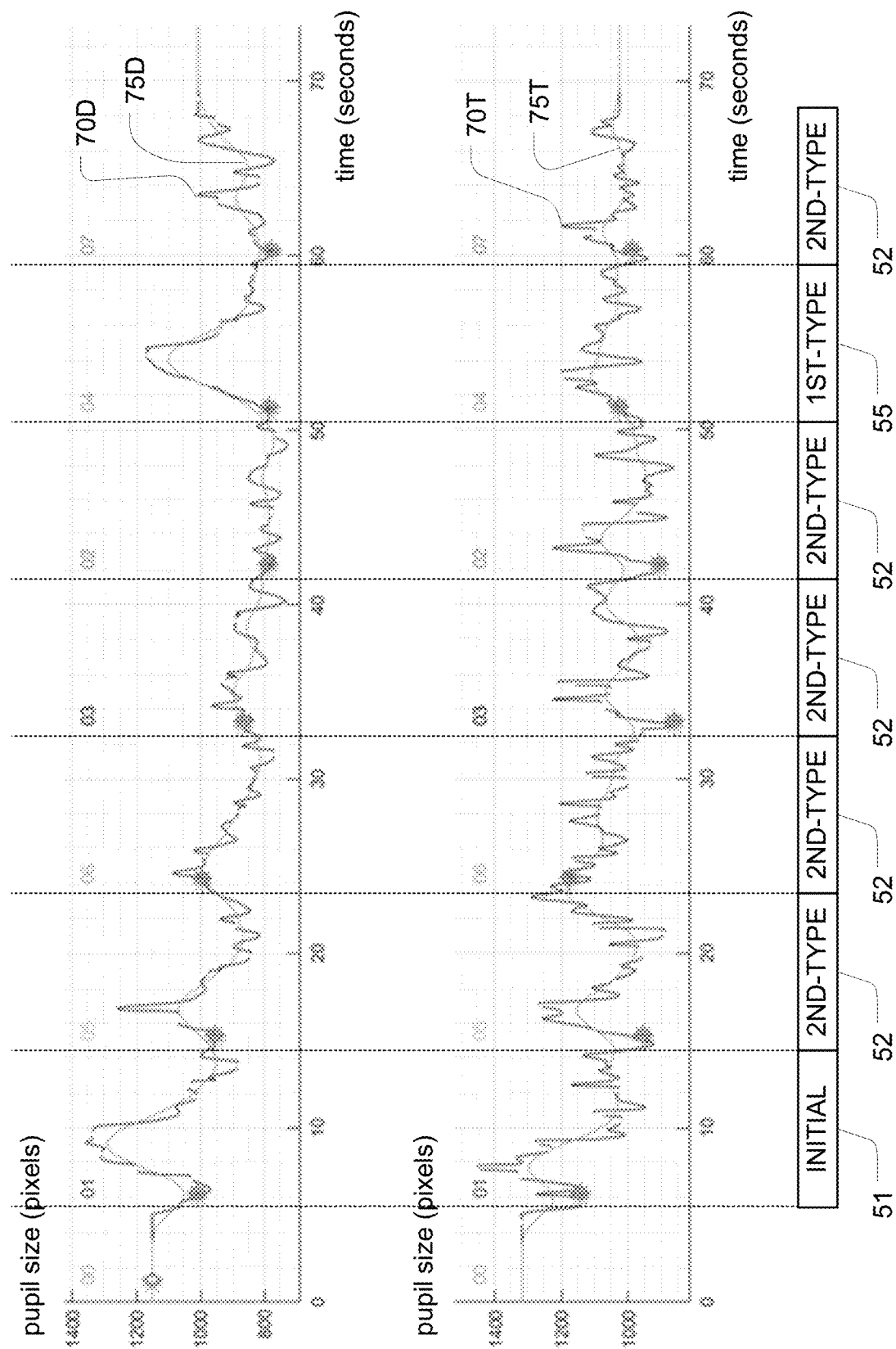
FIG. 5 depicts an example of changes in pupil size over time for a truthful testee and for a testee who is being deceptive.

FIG. 5 depicts one example of the changes in pupil size over time for a testee who is telling the truth (lower trace 70T) and for a testee who is being deceptive (upper trace 70D) in response to a sequence of sentences that includes an initial sentence 51, followed by 4 second-type sentences 52, followed by a first-type sentence 55, followed by one second-type sentence 52. The portions of each of the traces 70D and 70T that correspond to each of these sentences are demarcated by the labels on the bottom of FIG. 5 and the dashed vertical lines, and the large solid dots represent the start of the respective sentence. The X axes in FIG. 5 corresponds to time in seconds; and the Y axes in FIG. 5 corresponds to pupil size (measured in pixels). Traces 70D and 70T represent the measured pupil-sized data (after some preprocessing including low-pass filtering), and traces 75D and 75T represent the respective corresponding moving averages of the same data. These moving averages may be calculated, for example, by averaging the previous N samples, where N is an integer between 3 and 12. One suitable approach for evaluating the testee's pupil dilation response in all embodiments described herein is to measure the percentage increase in this moving average during the interval of time that corresponds to each sentence or word (depending on the context). In some embodiments, the moving average is calculated by averaging the previous 6 samples.

A testee's pupils will typically dilate significantly in response to the initial sentence 51 in any sequence, regardless of the content of that initial sentence. Accordingly, the pupil-size data that corresponds to the initial sentence is not used to evaluate whether the testee is being deceptive.

An examination of trace 75D for the deceptive testee reveals that the percentage increase in pupil size during the interval of time that corresponds to the first-type sentence 55 is larger than the percentage increase in pupil size during any of the intervals of time that correspond to the second-type sentences 52. In numeric terms, the moving average of the deceptive testee's pupil size increased about 35% (i.e., from 800 to 1100) in the interval of time that corresponds to the first-type sentence 55. But during each of the intervals of time that correspond to the second-type sentences 52, the increase in the moving average of the deceptive testee's pupil size was always less than 15%. Because the pupil-dilation response to the first-type sentence 55 is larger than the pupil-dilation response to each of the plurality of second-type sentences 52 for a deceptive testee, the system can use this relationship to evaluate whether a testee is being deceptive. For example, the system can (a) conclude that a testee's response to the first-type sentence 55 is deceptive when the system recognizes that the pupil-dilation response to the first-type sentence 55 is larger than the pupil-dilation response to each of the plurality of second-type sentences 52; and (b) conclude that a testee's response to the first-type sentence 55 is not deceptive when the pupil-dilation response to the first-type sentence 55 is not larger than the pupil-dilation response to each of the plurality of second-type sentences 52.

On the other hand, an examination of trace 75T for the truthful testee reveals that the percentage increase in pupil size during the interval of time that corresponds to the first-type sentence 55 is not larger than the percentage increase in pupil size during any of the intervals of time that correspond to the second-type sentences 52. In numeric terms, the increase in the moving average of the truthful testee's pupil size was less than 15% for the first-type sentence 55 and also for all of the second-type sentences 52. The system can therefore conclude that a testee's response to the first-type sentence 55 is truthful/not deceptive when the system recognizes that the pupil-dilation response to the first-type sentence 55 is not larger than the pupil-dilation response to the second-type sentences 52.

Returning now to FIGS. 1 and 2 (and, more specifically, to step S12 in FIG. 2), the processor/controller 20 monitors changes in the determined size of the testee's pupil during the outputting of the first-type sentence and the plurality of second-type sentences and during any responses to the first-type sentence and the plurality of second-type sentences made by the testee. As noted above, the processor/controller 20 executes image processing routines to determine the size of the testee's pupil in each frame of the images that include the testee's pupil.

In step S14, the processor/controller 20 compares changes in the determined size of the testee's pupil in response to the first-type sentence with changes in the determined size of the testee's pupil in response to the second-type sentences to ascertain whether a pupil-dilation response to the first-type sentence is larger than the pupil-dilation response to each of the plurality of second-type sentences. Based on this ascertaining, the processor/controller 20 outputs an indication of deceptiveness or non-deceptiveness in step S16. This may be accomplished, for example, by (a) outputting an indication of deceptiveness when the processor/controller 20 ascertains that the pupil-dilation response to the first-type sentence is larger than the pupil-dilation response to each of the plurality of second-type sentences, and/or (b) outputting an indication of non-deceptiveness when the processor/controller 20 ascertains that the pupil-dilation response to the first-type sentence is not larger than the pupil-dilation response to each of the plurality of second-type sentences.

When more than one first-type sentence is included in the set of sentences, the processor/controller 20 compares changes in the determined size of the testee's pupil in response to each of the first-type sentence with changes in the determined size of the testee's pupil in response to the second-type sentences to ascertain whether a pupil-dilation response to each individual first-type sentence is larger than the pupil-dilation response to each of the plurality of second-type sentences. Based on this ascertaining, the processor/controller 20 preferably outputs a respective indication of deceptiveness or non-deceptiveness for each individual first-type sentence.

The embodiments described herein rely on detecting a pupil-dilation response. But in situations where a testee's pupil is already very dilated, distinguishing the amount of dilation that results from the first-type sentence 55 from the amount of dilation that results from the second-type sentences 52 may be difficult. In these situations, it is preferable to activate a light source that increases the level of illumination that arrives at the testee's pupil. This will cause the testee's pupil to contract. After the testee's pupil has contracted, a larger amount of dilation will be possible. And this larger amount of dilation will make it easier to distinguish the amount of dilation that results from the first-type sentence 55 from the amount of dilation that results from the second-type sentences 52.

In some embodiments, the increase in illumination may persist for the duration of the testing session. This may be achieved, for example by having the processor/controller 20 send signals to the monitor 35 that cause the monitor 35 to display a bright image (see FIG. 1). in another example, the increase in illumination may be achieved by having the processor/controller 20 send signals (e.g., via Wi-Fi) to a smart outlet (not shown) into which a floor lamp has been plugged. When the smart outlet turns on, the floor lamp will turn on, which will increase the level of illumination that arrives at the testee's pupil.

In other embodiments, the increase in illumination may be transient. This may be achieved, for example by having the processor/controller 20 send signals to the monitor 35 that cause the monitor 35 to flash a short duration bright image (e.g., between 0.1 and 0.5 s) just prior to the time a given sentence is presented to the testee.

The embodiments described above in connection with FIG. 3-5 utilizes two different sentence types to evaluate whether a testee is being deceptive. More specifically, these examples utilize (1) a first-type sentence that is expected to evoke significant pupil dilation in a testee who is being deceptive and not to evoke significant pupil dilation in a testee who is not being deceptive, and (2) second-type sentences that are not expected to evoke significant pupil dilation in the testee. (The initial sentence is not relied on to evaluate whether a testee is being deceptive.) The embodiments described below in connection with FIG. 6-7 utilize these same two sentence types plus one third-type sentence type (referred to herein as an "third-type sentence") to evaluate whether or not a testee is being deceptive. The third-type sentence is expected to evoke significant pupil dilation in a testee who is not being deceptive. The third-type sentence may also evoke a response in deceptive testees, but in this case the pupil dilation response to first-type sentence will larger than the pupil dilation response to third-type sentence. And as described below, the third-type sentence improves the confidence of the evaluations made by the system both for determinations that a testee is being deceptive and for determinations that a testee is not being deceptive.

Figure 6:
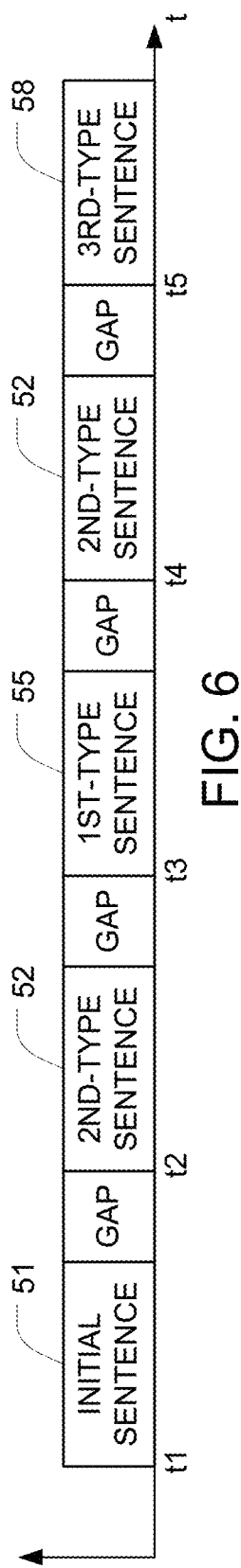
FIG. 6 depicts an exemplary time sequence for presenting a different set of sentences to the testee.

FIG. 6 depicts an example of a time sequence for presenting the set of sentences to the testee in these embodiments. More specifically, the initial sentence 51 is output prior to the first-type sentence 55, the plurality of second-type sentences 52, and the third-type sentence 58. But as between the latter three types 55, 52, and 58, the sequence is not critical. Note that in the example depicted in FIG. 6, there is only a single first-type sentence 55, only two second-type sentences 52, and only one third-type sentence 58. But in alternative examples, there could be more than one first-type sentence, more than two second-type sentences, and/or more than one third-type sentence.

Figure 7:
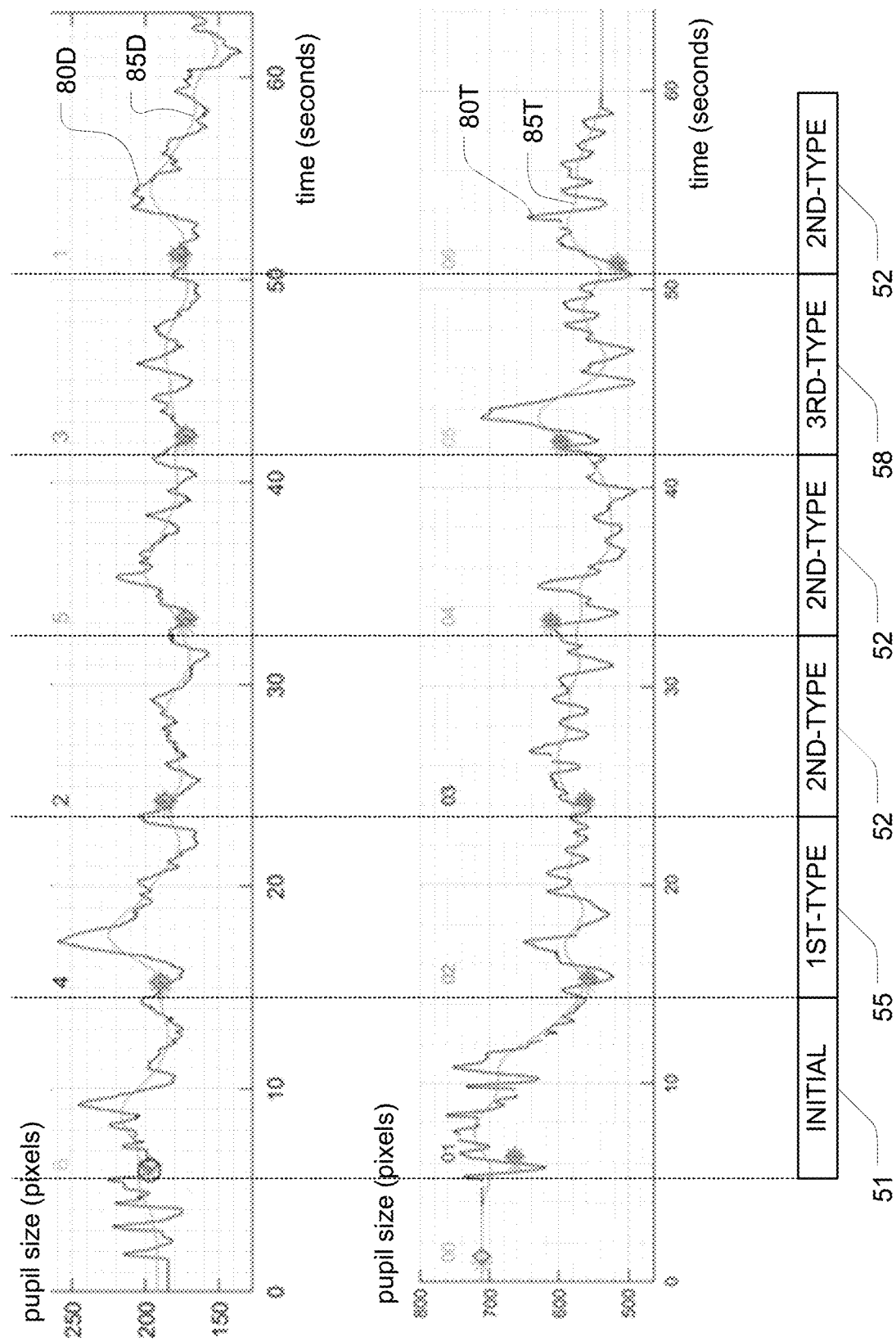
FIG. 7 depicts another example of changes in pupil size over time for a truthful testee and for a testee who is being deceptive.

Similar to the situation described above in connection with FIG. 5, the pupil-size data that corresponds to the initial sentence 51 is not used to evaluate whether the testee is being deceptive in this FIG. 6-7 embodiment.

The nature and content of the initial sentence 51, the first-type sentence 55, each of the second-type sentences 52, and the interrelationship between those types of sentences in this FIG. 6-7 embodiment is the same as described above in connection with FIG. 3-5. But notably, the language, grammatical structure, duration, volume, tone, voice, complexity, and language style of the third-type sentence does not have to be similar to the first-type sentence. If the third-type sentence has a keyword, the position of the keyword does not have to be similar to the position of the keyword in the first-type sentence. Furthermore, the third-type sentence may not even have a keyword at all.

The main requirement of the third-type sentence is that it should evoke significant pupil dilation in a testee who is not being deceptive. The third-type sentence may or may not evoke significant pupil dilation in a testee who is being deceptive. One example of a suitable third-type sentence is a sentence that is output in a different language than all the first-type and second-type sentences. For example, in a situation where the first-type sentence and all the second-type sentences are output in English, the third-type sentence could be output in German. The German sentence will induce more cognitive load than the English sentences, and will therefore cause a larger pupil size response from a non-deceptive testee (as compared to the first-type and second-type sentences). Another example of a suitable third-type sentence is a sentence that is significantly louder than the first-type sentence and all the second-type sentences. The louder sentence will increase the testee's emotional load, and will therefore cause a larger pupil size response from a non-deceptive testee (as compared to the first-type and second-type sentences). Yet another example of a suitable third-type sentence is a sentence that is expected to evoke significant pupil dilation based on its content. Examples of content that can evoke significant pupil dilation include absurd statements (e.g., "why aren't you wearing underpants today?"), insults (e.g., "your shirt is exceptionally ugly"), jokes, etc. The content will increase the testee's emotional load, and will therefore cause a larger pupil size response from a non-deceptive testee (as compared to the first-type and second-type sentences).

When third-type sentence is presented to a deceptive testee, it may also evoke significant pupil dilation. But because the deceptive testee's response to the first-type sentence actually has consequences (e.g., getting arrested, not getting a job, etc.), their pupil dilation response to the first-type sentence is expected to be larger than their pupil dilation response to the third-type sentence. Note that in some cases, particularly when the third-type sentence arrives after the first-type sentence, the third-type sentence may not evoke significant pupil dilation in a deceptive testee.

FIG. 7 depicts one example of the changes in pupil size over time for a testee who is telling the truth (lower trace 80T) and for a testee who is being deceptive (upper trace 80D) in response to a sequence of sentences that includes an initial sentence 51, followed by a first-type sentence 55, two second-type sentences 52, followed by a third-type sentence 58, followed by one second-type sentence 52. The portions of each of the traces 80D and 80T that correspond to each of these sentences are demarcated by the labels on the bottom of FIG. 7 and the dashed vertical lines. The X axes in FIG. 7 corresponds to time in seconds; and the Y axes in FIG. 7 correspond to pupil size (measured in pixels). Traces 80D and 80T represent the measured pupil-sized data (after some preprocessing including low-pass filtering), and traces 85D and 85T represent the respective corresponding moving averages of the same data, which may be calculated using any of the approaches described above in connection with FIG. 5. The difference in scale of the Y axes (between the lower traces 80T/85T and the upper traces 80D/80T) is attributable to the different pupil sizes of two different individual testees.

The third-type sentence 58 that is added in the FIG. 6-7 embodiments can provide an advantage with respect to the FIG. 3-5 embodiments by improving the confidence of the evaluations made by the system, both for determinations that a testee is being deceptive and for determinations that a testee is not being deceptive.

Improving the confidence of evaluations in those situations where the testee is being deceptive is best understood by comparing trace 75D in FIG. 5 (which does not include a third-type sentence) with trace 85D in FIG. 7 (which does include a third-type sentence). In these FIG. 6-7 embodiments, the processor/controller 20 compares changes in the determined size of the testee's pupil in response to the first-type sentence 55 with changes in the determined size of the testee's pupil in response to the second-type sentences 52. This is done to ascertain whether a pupil-dilation response to the first-type sentence 55 is larger than the pupil-dilation response to each of the plurality of second-type sentences 52 (which is the case for trace 80D depicted in FIG. 7). So far, this is similar to the FIG. 3-5 embodiment. But in addition, the processor/controller 20 in the FIG. 6-7 embodiments compares changes in the testee's pupil size in response to the third-type sentence 58 with changes in the testee's pupil size in response to the first-type sentence 55. This is done to ascertain whether a pupil-dilation response to the first-type sentence 55 is larger than a pupil-dilation response to the third-type sentence 58 (which is also the case for trace 80D).

In the FIG. 6-7 embodiments, an output indicating deceptiveness is generated when the processor/controller 20 ascertains that a pupil-dilation response to the first-type sentence 55 is larger than the pupil-dilation response to each of the plurality of second-type sentences 52 and also larger than the pupil-dilation response to the third-type sentence 58 (which is the case for trace 80D). These embodiments advantageously improve the confidence of a "deceptiveness" output with respect to the confidence of the FIG. 3-5 embodiments discussed above. larger pupil-dilation response to the first-type sentence 55 as compared to the third-type sentence 58 is expected from a deceptive testee because the first-type sentence is expected to have a stronger impact on a deceptive testee than the third-type sentence. This stronger impact is expected because there will usually be significant and/or unpleasant consequences associated with deception with regard to the first-type sentence (e.g., shame, failure, being charged with a crime, not getting a job, etc.).

Improving the confidence of evaluations in those situations where the testee is not being deceptive is best understood by comparing trace 75T in FIG. 5 (which does not include a third-type sentence) with trace 85T in FIG. 7 (which does include a third-type sentence). More specifically, an examination of trace 85T for the truthful testee reveals that the percentage increase in pupil size during the interval of time that corresponds to the third-type sentence 58 is larger than the percentage increase in pupil size during any of the intervals of time that correspond to the second-type sentences 52, and is also larger than the percentage increase in pupil size during the first-type sentence interval 55.

In these FIG. 6-7 embodiments, in addition to comparing the responses to the first-type sentence to the responses to the second-type sentences (as described above), the processor/controller 20 also compares changes in the testee's pupil size in response to the third-type sentence 58 with changes in the testee's pupil size in response to the first-type sentence 55. An output indicating non-deceptiveness is generated when either (i) the processor/controller 20 ascertains that a pupil-dilation response to the third-type sentence 58 is larger than the pupil-dilation response to the first-type sentence 55 (which is the case for trace 80T), or (ii) when the processor/controller 20 ascertains that the pupil-dilation response to the first-type sentence is not larger than the pupil-dilation response to each of the plurality of second-type sentences. (Condition (ii) is similar to the situation described above in connection with FIGS. 2-5.) These embodiments advantageously improve the reliability of a "non-deceptiveness" output with respect to the FIG. 3-5 embodiments discussed above.

The embodiments described above in connection with FIGS. 1-7 include at least one "first-type sentence" (which is a sentence that the party administering the test cares about) and a plurality of "second-type sentences" which are used as a baseline against which to compare the testee's response to the first-type sentence.

Figure 8:
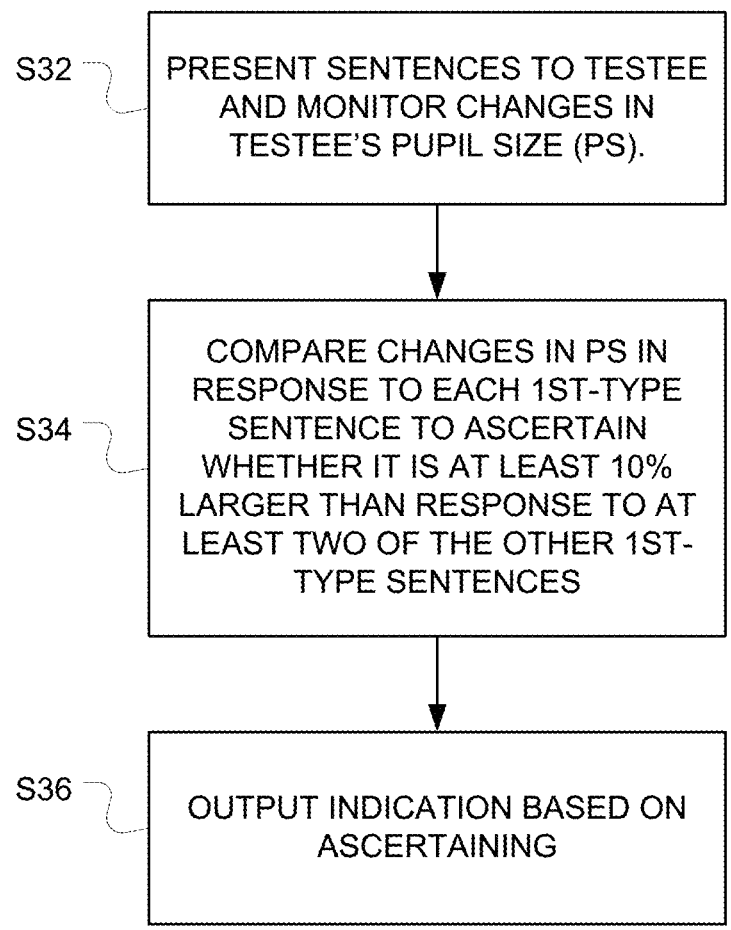
FIG. 8 is a flowchart for presenting an other set of sentences to a testee, and evaluating deceptiveness by monitoring changes in the size of the testee's pupil.
Figure 9:
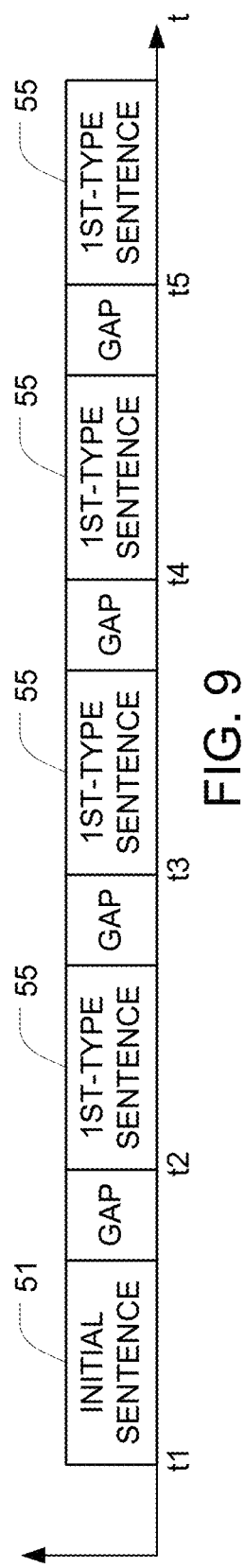
FIG. 9 depicts an example of a time sequence for presenting the set of words to the testee in the FIG. 8 embodiment.

FIGS. 8 and 9 depict an example that relies on a different approach for evaluating whether a testee is being deceptive. In this approach, the set of sentences that is presented includes at least three first-type sentences. As in the FIG. 1-7 embodiments, each of the first-type sentences is expected to evoke significant pupil dilation in a testee who is being deceptive and not to evoke significant pupil dilation in a testee who is not being deceptive. But notably, this embodiment does not require any second-type sentences to evaluate whether a testee is being deceptive. In these embodiments, the set of sentences includes an initial sentence 51 and at least three first-type sentences 55. The initial sentence 51 is output prior to all of the first-type sentences 55.

Assume, for example, that a customs agent wants to screen people who are about to enter a country. In this situation, the party administering the test could ask the following questions: (1) What flight did you arrive on? (2) Did you bring any fruits or vegetables? (3) Did you bring any plants or seeds? (4) Did you bring any animals or insects? (5) Have you recently been on a farm or ranch? (6) Are you carrying more than $10,000 in currency? (7) Did you bring any cigarettes with you? (8) Did you bring any alcoholic beverages? (9) Did you bring any drugs? In this situation, the customs agent presumably cares about whether the testee is being deceptive in response to questions #2-9, and wants to evaluate whether the testee is being deceptive for all those questions. Therefore, in this example, question #1 is the initial sentence 51, and all of the other questions #2-9 qualify as first-type sentences 55.

When the number of questions is sufficiently large, it is reasonable to assume that the answer to at least two of the questions will truthfully be "no," and for those questions, significant pupil dilation is not expected to be evoked in the testee. In this situation, the testee's non-deceitful responses serve as the baseline against which the testee's response to the other questions are compared. One suitable approach for selecting the sentences that will be used as a baseline for comparison is to evaluate the pupil-dilation response to each of the sentences, and select the two sentences that give rise to the smallest pupil-dilation response as a baseline against which the remaining pupil-dilation responses will be compared. For the remaining questions, evocation of significant pupil dilation is expected if the testee is being deceptive and not expected if the testee is not being deceptive.

The FIG. 1 hardware block diagram and the description of that figure above applies with equal force to this FIG. 8-9 embodiment.

The probability of success in evaluating whether a testee is being deceptive can be improved significantly by making the first-type sentences 55 similar to each other in a number of important regards. More specifically, the first-type sentences are all in the same language; their average volumes are all within 10 dB of each other; and each of them has a duration of less than five seconds. Optionally, each of the first-type sentences 55 may be made similar to each other in additional ways (e.g., as described above in connection with the FIG. 1-7 embodiments).

Gaps of at least three seconds are interposed between adjacent sentences (e.g., as described above in connection with the FIG. 1-7 embodiments).

Turning now to FIG. 8, in step S32 the set of sentences 51-55 is presented to the testee, and the system evaluates whether the testee is being deceptive by monitoring changes in the determined size of the testee's pupil (e.g., using an appropriate program or programs running on the processor/controller 20 depicted in FIG. 1).

The processor/controller 20 controls the audio circuit 30 so that the audio circuit outputs an audio signal corresponding to a set of sentences. The speaker 32 converts the audio signal to sounds that are presented to the testee. The set of sentences includes an initial sentence, and at least three first-type sentences. The sentences can be in the form of questions, statements, or any other form.

As described above in connection with the FIG. 1-7 embodiments, a "first-type sentence" is a sentence that the party administering the test cares about, and the evaluation of whether a testee is being deceptive applies to the first-type sentences. Each first-type sentence is expected to evoke significant pupil dilation in a testee who is being deceptive and not to evoke significant pupil dilation in a testee who is not being deceptive.

The processor/controller 20 monitors changes in the determined size of the testee's pupil during the outputting of the first-type sentences and during any responses to the first-type sentences made by the testee. The processor/controller 20 executes image processing routines to determine the size of the testee's pupil in each frame of the images that include the testee's pupil.

In step S34, The processor/controller 20 compares changes in the determined size of the testee's pupil in response to each of the first-type sentences to ascertain whether a pupil-dilation response to each respective one of the first-type sentences is at least 10% larger than a pupil-dilation response to at least two of the other first-type sentences.

Based on this ascertaining, in step S36 the processor/controller 20 outputs an indication of deceptiveness or non-deceptiveness for at least one of the first-type sentences. This may be accomplished, for example, by (a) outputting an indication of deceptiveness for a respective one of the first-type sentences when the processor/controller 20 ascertains that the pupil-dilation response to the respective first-type sentence is at least 10% larger than a pupil-dilation response to at least two of the other first-type sentences, and/or (b) outputting an indication of non-deceptiveness when the processor/controller 20 ascertains that no pupil-dilation response to any given one of the first-type sentences is at least 10% larger than a pupil-dilation response to at least two of the other first-type sentences.

Optionally, this FIG. 8-9 embodiment may also utilize a third-type sentence to improve the confidence of the evaluations made by the system. The third-type sentence in this FIG. 8-9 embodiment is similar to the third-type sentence described above in the FIG. 1-7 embodiment, and it is expected to evoke significant pupil dilation in a testee who is not being deceptive.

When the optional third-type sentence is utilized, in addition to comparing the responses to the first-type sentences (as described above), the processor/controller 20 also compares changes in the testee's pupil size in response to the third-type sentence with changes in the testee's pupil size in response to each of the first-type sentences. The processor/controller 20 outputs an indication of deceptiveness for a respective one of the first-type sentences when the processor/controller 20 ascertains that the pupil-dilation response to the respective first-type sentence is at least 10% larger than the pupil-dilation response to at least two of the other first-type sentences and is also larger than the pupil-dilation response to the third-type sentence. The processor/controller 20 outputs an indication of non-deceptiveness when the processor/controller 20 ascertains that the pupil-dilation response to each of the first-type sentences is smaller than the pupil-dilation response to the third-type sentence, or when the processor/controller 20 ascertains that the pupil-dilation response to none of the first-type sentences is at least 10% larger than the pupil-dilation response to at least two other first-type sentences.

Figure 10:
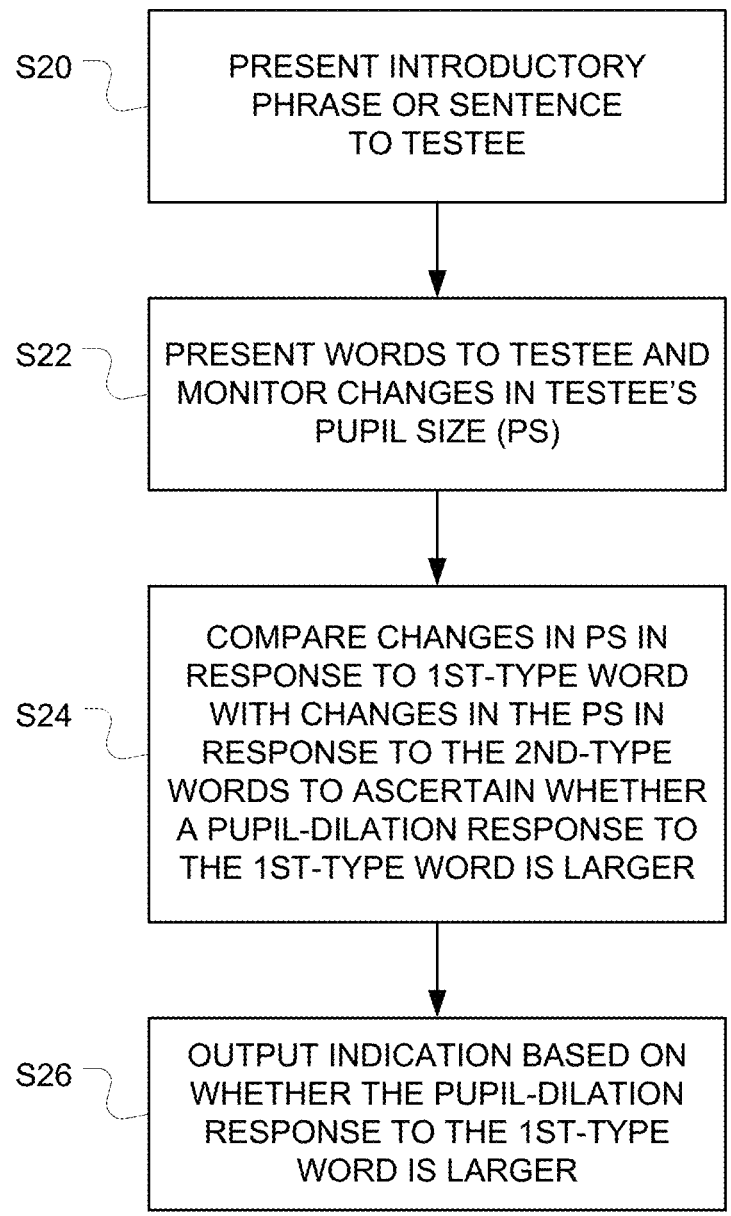
FIG. 10 is a flowchart for presenting a set of words to a testee, and evaluating deceptiveness by monitoring changes in size of the testee's pupil.
Figure 11:
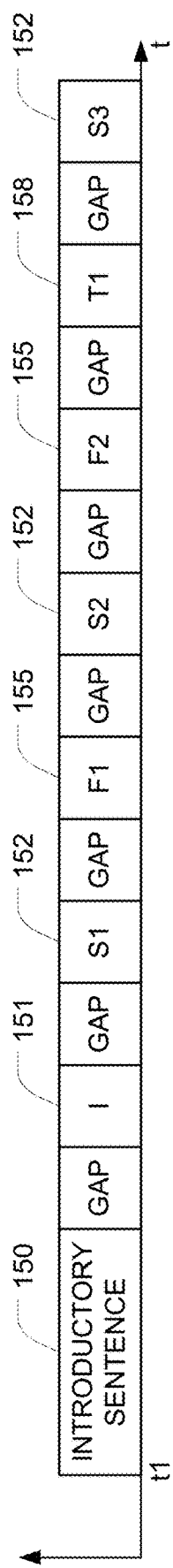
FIG. 11 depicts an example of a time sequence for presenting the set of words to the testee in the FIG. 10 embodiment.

In the embodiments described above in connection with FIG. 1-9, a set of sentences (e.g., questions) are presented to the testee, and changes in the testee's pupil size are monitored. The embodiments described below in connection with FIG. 10-11 are similar, but instead of presenting a set of sentences, a set of words are presented to the testee. The FIG. 1 hardware block diagram applies with equal force to the FIG. 10-11 embodiments.

FIG. 10 depicts a flowchart for an embodiment in which a set of words is presented to the testee, and the system evaluates whether the testee is being deceptive by monitoring changes in the determined size of the testee's pupil. The steps S20-S26 of this flowchart are implemented by an appropriate program or programs running on the processor/controller 20 depicted in FIG. 1.

First, in step S20, the processor/controller 20 controls the audio circuit 30 so that the audio circuit outputs an audio signal corresponding to an introductory phrase or sentence. The speaker 32 converts the audio signal to sounds that are presented to the testee. When an introductory sentence is used, it could be a question (e.g., "What do you think of the following things?) or a statement (e.g., "We are going to monitor your reaction to the following items").

Next, in step S22, the processor/controller 20 controls the audio circuit 30 so that the audio circuit outputs an audio signal corresponding to a set of words. The speaker 32 converts the audio signal to sounds that are presented to the testee. The set of words includes an initial word, a first-type word, and a plurality of second-type words.

A "first-type word" is a word that the party administering the test cares about, and the evaluation of whether a testee is being deceptive applies to the first-type word. The "second-type word(s)" and "third-type word(s)" described below are presented to the testee so that the system has a baseline against which to compare the testee's response to the first-type word, with the ultimate goal of evaluating whether the testee is being deceptive with respect to the first-type word. The first-type word, the second-type word, and third-type word correspond to the first-type sentence, second-type sentence, and third-type sentence in the FIG. 2-9 embodiments described above, but the former are words instead of sentences.

The first-type word is expected to evoke significant pupil dilation in a testee who is being deceptive and not to evoke significant pupil dilation in a testee who is not being deceptive. Each of the second-type words is not expected to evoke significant pupil dilation in the testee (although pupil dilation may, in fact, occur, depending on the content of the word).

FIG. 11 depicts an example of a time sequence for presenting the set of words to the testee. More specifically, the introductory sentence 150 is presented first. Then, the initial word 151 is output prior to the first-type word 155 and the plurality of second-type words 152. But as between the first-type word and the second-type words 152, the sequence is not critical. Note that in the example depicted in FIG. 11, there are two first-type words 155 and three second-type words 152. But in alternative examples, there could be a different number of first-type words and/or second-type words.

Gaps of at least 2 s interposed between words within the set. In some embodiments, these gaps will all have the same duration. But in other embodiments, the size of the gaps may vary (e.g., as described above in connection with the FIG. 1-9 embodiment). The entire set of words is presented to the testee in less than 2 minutes, and the set of words contains less than 20 words.

As in the embodiment described above in connection with FIG. 1-9, the probability of success in evaluating whether a testee is being deceptive can be improved significantly by making the first-type word 155 and the second-type words 152 similar to each other in a number of important regards. More specifically, the first-type word and each of the second-type words should all be in the same language (i.e., all of the words could be in English; or all of the words could be in French); and the average volume of each of the second-type words should be within 10 dB of the average volume of the first-type word.

Making the first-type word each of the second-type words similar to each other in these ways increases the probability that the pupil-dilation response observed by the system is attributable to the content of those words as opposed to other factors including but not limited to cognitive load, emotional load, etc. And this can advantageously increase the probability of success in evaluating whether a testee is being deceptive.

Optionally, the first-type word 155 and the second-type words 152 may be made similar to each other in additional ways, which can further improve the probability of success in evaluating whether a testee is being deceptive. In some embodiments, this is accomplished by outputting the first-type word and each of the second-type words in the same voice and/or making them similar to each other in the level of complexity and language style. The peak volume of each of the second-type words may optionally also be set to be within 10 dB of the peak average volume of the first-type word. Making the first-type word each of the second-type words similar to each other in one or more of these additional ways can further increases the probability that the pupil-dilation response observed by the system is attributable to the content of those words as opposed to other factors, which can further increase the probability of success in evaluating whether a testee is being deceptive.

Returning now to FIGS. 10 and 11 (and, more specifically, to step S22 in FIG. 10), the processor/controller 20 monitors changes in the determined size of the testee's pupil during the outputting of the first-type word and the plurality of second-type words and during any responses to the first-type word and the plurality of second-type words made by the testee. As noted above, the processor/controller 20 executes image processing routines to determine the size of the testee's pupil in each frame of the images that include the testee's pupil.

In step S24, the processor/controller 20 compares changes in the determined size of the testee's pupil in response to the first-type word with changes in the determined size of the testee's pupil in response to the second-type words to ascertain whether a pupil-dilation response to the first-type word is larger than the pupil-dilation response to each of the plurality of second-type words. Based on this ascertaining, the processor/controller 20 outputs an indication of deceptiveness or non-deceptiveness in step S26. This may be accomplished, for example, by (a) outputting an indication of deceptiveness when the pupil-dilation response to the first-type word is larger than the pupil-dilation response to each of the plurality of second-type words, and/or (b) outputting an indication of non-deceptiveness when the pupil-dilation response to the first-type word is not larger than the pupil-dilation response to each of the plurality of second-type words.

Optionally, a light source that increases the level of illumination that arrives at the testee's pupil may be activated, as described above in connection with the FIG. 1-9 embodiment.

The embodiments described above in connection with FIG. 10-11 utilizes two different word types to evaluate whether a testee is being deceptive. More specifically, these examples utilize (1) a first-type word that is expected to evoke significant pupil dilation in a testee who is being deceptive and not to evoke significant pupil dilation in a testee who is not being deceptive, and (2) second-type words that are not expected to evoke significant pupil dilation in the testee. (The initial word is not relied on to evaluate whether a testee is being deceptive.) Optionally, an additional word type (referred to herein as an "third-type word") may be added to evaluate whether a testee is being deceptive. The third-type word 158 is expected to evoke significant pupil dilation in a testee who is not being deceptive, and it operates in the same way as the third-type sentence 58 described above in connection with the FIG. 1-9 embodiments.

The embodiments described above in connection with FIGS. 10-11 include at least one first-type word and a plurality of second-type words (which are used as a baseline against which to compare the testee's response to the first-type word). In alternative embodiments, only first-type words are used, and these embodiments are analogous to the embodiments described above in connection with FIG. 8-9 that relied on only first-type sentences. More specifically, when the number of first-type words is sufficiently large, it is reasonable to assume that the testee will not be deceptive with regard to all of the words. And for those words, significant pupil dilation is not expected to be evoked in the testee. In this situation, the testee's non-deceitful responses serve as the baseline against which the testee's response to the other words are compared. One suitable approach for selecting the words that will be used as a baseline for comparison is to evaluate the pupil-dilation response to each of the words, and select the two words that give rise to the smallest pupil-dilation response as a baseline against which the remaining pupil-dilation responses will be compared. For the remaining words, evocation of significant pupil dilation is expected if the testee is being deceptive and not expected if the testee is not being deceptive.

The FIG. 1 hardware block diagram and the description of that figure above applies with equal force to this embodiment.

The processor/controller 20 controls the audio circuit 30 so that the circuit outputs an audio signal corresponding to (a) an introductory phrase or sentence and (b) a set of words. The set of words is output after the introductory phrase or sentence, with gaps of at least 2 s interposed between words within the set. The set of words includes an initial word and at least three first-type words, and each of the first-type words is expected to evoke significant pupil dilation in a testee who is being deceptive and not to evoke significant pupil dilation in a testee who is not being deceptive. The initial word is presented to the testee prior to the presenting of the first-type words, the entire set of words is presented to the testee in less than 2 minutes, and the set of words contains less than 20 words. All the first-type words are in the same language, and the first-type words all have volumes within 10 dB of each other.

The processor/controller 20 monitors changes in the testee's pupil size during the presenting of the first-type words and during any responses to the first-type words made by the testee. The processor/controller 20 compares changes in the testee's pupil size in response to each of the first-type words to ascertain whether a pupil-dilation response to each respective one of the first-type words is at least 10% larger than a pupil-dilation response to at least two of the other first-type words, and outputs an indication of deceptiveness or non-deceptiveness for at least one of the first-type words based on a result of the ascertaining. This may be implemented, for example, by (a) outputting an indication of deceptiveness for a respective one of the first-type words when the pupil-dilation response to any given one of the respective first-type words is at least 10% larger than a pupil-dilation response to at least two of the other first-type words, and/or (b) outputting an indication of non-deceptiveness when no pupil-dilation response to any given one of the first-type words is at least 10% larger than a pupil-dilation response to at least two of the other first-type words.

Optionally, these embodiments may also utilize a third-type word to improve the confidence of the evaluations made by the system. The third-type word is expected to evoke significant pupil dilation in a testee who is not being deceptive. In these embodiments, in addition to comparing the responses to the first-type words (as described above) the processor/controller 20 compares changes in the testee's pupil size in response to the third-type word with changes in the testee's pupil size in response to each of the first-type words. The processor/controller 20 outputs an indication of deceptiveness for a respective one of the first-type words when the pupil-dilation response to the respective first-type word is at least 10% larger than the pupil-dilation response to at least two of the other first-type words and is also larger than the pupil-dilation response to the third-type word. The processor/controller 20 outputs an indication of non-deceptiveness (i) when the pupil-dilation response to each of the first-type words is smaller than the pupil-dilation response to the third-type word or (ii) when the pupil-dilation response to none of the first-type words is at least 10% larger than the pupil-dilation response to at least two other first-type words.

In today's difficult times, terrorism, crime and deception are unfortunately a daily concern of citizens of most countries around the globe. It has many faces: cybercrime, suicide bombers, airplane hijacking, murder, theft, fraud, embezzlement, industrial espionage, etc. The embodiments described herein can provide important tools for fighting all of these concerns. Such technologies are advantageously applicable to a dual market: the security/government market (HLS, TSA, military, law enforcement, security agencies, government) and the private sector (investigators, lawyers, technology & business companies, health care, insurance, HR, banks, trade floors, and more).

The techniques described herein are also useful as a tool for investigation and for screening. As a screening tool, the technologies described herein can be used for pre-employment checks for candidates and periodic credibility checks for employees in both markets (security/government and private). In addition, the techniques described herein can facilitate high throughput screening, which can be very beneficial in screening crowds at entrances to establishments, borders, and airports for a variety of purposes (e.g., age verification, counter terrorism, or routine screening at customs checkpoints).

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus for evaluating whether a testee is being deceptive, the apparatus comprising:
   an image sensor configured to capture a plurality of sequential images of the testee's pupil;
   a processor configured to determine a size of the testee's pupil in the plurality of sequential images;
   a circuit that generates an audio output; and
   a controller programmed to control the circuit so that the circuit outputs an audio signal corresponding to a set of sentences, wherein the set of sentences includes an initial sentence, a first-type sentence, and a plurality of second-type sentences, wherein the first-type sentence is expected to evoke significant pupil dilation in a testee who is being deceptive and not to evoke significant pupil dilation in a testee who is not being deceptive, wherein each of the second-type sentences is not expected to evoke significant pupil dilation in the testee, and wherein the initial sentence is output prior to the outputting of the first-type sentence and the plurality of second-type sentences,
   wherein the controller is further programmed to monitor changes in the determined size of the testee's pupil during the outputting of the first-type sentence and the plurality of second-type sentences and during any responses to the first-type sentence and the plurality of second-type sentences made by the testee, wherein the controller is further programmed to compare changes in the determined size of the testee's pupil in response to the first-type sentence with changes in the determined size of the testee's pupil in response to the second-type sentences to ascertain whether a pupil-dilation response to the first-type sentence is larger than a pupil-dilation response to each of the plurality of second-type sentences, and wherein the controller is further programmed to output an indication of deceptiveness or non-deceptiveness based on the ascertaining of whether the pupil-dilation response to the first-type sentence is larger than the pupil-dilation response to each of the plurality of second-type sentences, wherein the first-type sentence and each of the second-type sentences are all in the same language, wherein the average volume of each of the portions of the audio signal that corresponds to a second-type sentence is within 10 dB of the average volume of the portion of the audio signal that corresponds to the first-type sentence, wherein the first-type sentence and each of the second-type sentences has a duration of less than 5 s, and wherein gaps of at least 3 s are interposed between adjacent sentences within the set of sentences.

2. The apparatus of claim 1, wherein the controller is further programmed to (a) output an indication of deceptiveness when the controller ascertains that the pupil-dilation response to the first-type sentence is larger than the pupil-dilation response to each of the plurality of second-type sentences, and (b) output an indication of non-deceptiveness when the controller ascertains that the pupil-dilation response to the first-type sentence is not larger than the pupil-dilation response to each of the plurality of second-type sentences.

3. The apparatus of claim 1, wherein portions of the audio signal corresponding to the first-type sentence and the plurality of second-type sentences are output using the same voice, wherein the entire set of sentences is output within 2 minutes, and wherein the set of sentences that is output contains between 4 and 10 sentences.

4. The apparatus of claim 1, wherein the controller is further programmed to ascertain whether a pupil-dilation response to the first-type sentence is at least 10% larger than a pupil-dilation response to each of the plurality of second-type sentences.

5. The apparatus of claim 1, further comprising an audio amplifier and a speaker, wherein the audio amplifier receives the audio output from the circuit, and wherein an output of the audio amplifier drives the speaker.

6. The apparatus of claim 1, further comprising a light source configured to control a level of illumination that arrives at the testee's pupil in response to instructions received from the controller, wherein the controller is further programmed to send the instructions to the light source.

7. The apparatus of claim 1, wherein a single integrated circuit serves as both the processor and the controller.

8. The apparatus of claim 1, wherein the set of sentences further includes a third-type sentence that is expected to evoke significant pupil dilation in a testee who is not being deceptive, and wherein the controller is further programmed to (a) compare changes in the testee's pupil size in response to the third-type sentence with changes in the testee's pupil size in response to the first-type sentence to ascertain whether a pupil-dilation response to the first-type sentence is larger than a pupil-dilation response to the third-type sentence, (b) output an indication of deceptiveness when the controller ascertains that the pupil-dilation response to the first-type sentence is larger than the pupil-dilation response to each of the plurality of second-type sentences and is also larger than the pupil-dilation response to the third-type sentence, and (c) output an indication of non-deceptiveness when the controller ascertains that the pupil-dilation response to the third-type sentence is larger than the pupil-dilation response to the first-type sentence or when the controller ascertains that the pupil-dilation response to the first-type sentence is not larger than the pupil-dilation response to each of the plurality of second-type sentences.

9. The apparatus of claim 1, wherein the grammatical structure, duration, level of complexity, and language style of each of the second-type sentences is similar to the grammatical structure, duration, level of complexity, and language style of the first-type sentence.

10. The apparatus of claim 1, wherein the first-type sentence includes a material keyword, wherein each of the second-type sentences includes a respective other keyword, and wherein the position of the respective other keyword within each of the second-type sentences is similar to the position of the material keyword within the first-type sentence, wherein any two given keywords are deemed to have a similar position within a respective sentence when the two given keywords are either (a) both positioned in the initial one-third of the respective sentence, (b) both positioned in the middle one-third of the respective sentence, or (c) both positioned in the last one-third of the respective sentence.

11. A method of evaluating whether a testee is being deceptive, the method comprising:

presenting a set of sentences to the testee, wherein the set of sentences includes an initial sentence, a first-type sentence, and a plurality of second-type sentences, wherein the first-type sentence is expected to evoke significant pupil dilation in a testee who is being deceptive and not to evoke significant pupil dilation in a testee who is not being deceptive, wherein each of the second-type sentences is not expected to evoke significant pupil dilation in the testee, and wherein the initial sentence is presented to the testee prior to the presenting of the first-type sentence and the plurality of second-type sentences;

monitoring changes in the testee's pupil size during the presenting of the first-type sentence and the plurality of second-type sentences and during any responses to the first-type sentence and the plurality of second-type sentences made by the testee;

comparing changes in the testee's pupil size in response to the first-type sentence with changes in the testee's pupil size in response to the second-type sentences to ascertain whether a pupil-dilation response to the first-type sentence is larger than a pupil-dilation response to each of the plurality of second-type sentences; and outputting an indication of deceptiveness or non-deceptiveness based on the ascertaining of whether the pupil-dilation response to the first-type sentence is larger than the pupil-dilation response to each of the plurality of second-type sentences, wherein the first-type sentence and each of the second-type sentences are all in the same language, wherein the average volume of each of the second-type sentences is within 10 dB of the average volume of the first-type sentence, wherein the first-type sentence and each of the second-type sentences has a duration of less than 5 s, and wherein gaps of at least 3 s are interposed between adjacent sentences within the set of sentences.

12. The method of claim 11, wherein the outputting comprises (a) outputting an indication of deceptiveness when the comparing reveals that the pupil-dilation response to the first-type sentence is larger than the pupil-dilation response to each of the plurality of second-type sentences, and (b) outputting an indication of non-deceptiveness when the comparing reveals that the pupil-dilation response to the first-type sentence is not larger than the pupil-dilation response to each of the plurality of second-type sentences.

13. The method of claim 11, wherein the first-type sentence and the plurality of second-type sentences are all in the same voice, wherein the entire set of sentences is presented to the testee within 2 minutes, and wherein the set of sentences that is presented to the testee contains between 4 and 10 sentences.

14. The method of claim 11, further comprising controlling a level of illumination that arrives at the testee's pupil.

15. The method of claim 11, wherein the set of sentences further includes a third-type sentence that is expected to evoke significant pupil dilation in a testee who is not being deceptive, and wherein the method further comprises (a) comparing changes in the testee's pupil size in response to the third-type sentence with changes in the testee's pupil size in response to the first-type sentence to ascertain whether a pupil-dilation response to the first-type sentence is larger than a pupil-dilation response to the third-type sentence, (b) outputting an indication of deceptiveness when a pupil-dilation response to the first-type sentence is larger than the pupil-dilation response to each of the plurality of second-type sentences and is also larger than the pupil-dilation response to the third-type sentence, and (c) outputting an indication of non-deceptiveness when the pupil-dilation response to the third-type sentence is larger than the pupil-dilation response to the first-type sentence or when the pupil-dilation response to the first-type sentence is not larger than the pupil-dilation response to each of the plurality of second-type sentences.

16. The method of claim 11, wherein the grammatical structure, duration, level of complexity, and language style of each of the second-type sentences is similar to the grammatical structure, duration, level of complexity, and language style of the first-type sentence.

17. The method of claim 11, wherein the first-type sentence includes a material keyword, wherein each of the second-type sentences includes a respective other keyword, and wherein the position of the respective other keyword within each of the second-type sentences is similar to the position of the material keyword within the first-type sentence, wherein any two given keywords are deemed to have a similar position within a respective sentence when the two given keywords are either (a) both positioned in the initial one-third of the respective sentence, (b) both positioned in the middle one-third of the respective sentence, or (c) both positioned in the last one-third of the respective sentence.

18. An apparatus for evaluating whether a testee is being deceptive, the apparatus comprising:

an image sensor configured to capture a plurality of sequential images of the testee's pupil;

a processor configured to determine a size of the testee's pupil in the plurality of sequential images;

a circuit that generates an audio output; and a controller programmed to control the circuit so that the circuit outputs an audio signal corresponding to (a) an introductory phrase or sentence and (b) a set of words, wherein the set of words is output after the introductory phrase or sentence, with gaps of at least 2 s interposed between words within the set, wherein the set of words includes an initial word, a first-type word, and a plurality of second-type words, wherein the first-type word is expected to evoke significant pupil dilation in a testee who is being deceptive and not to evoke significant pupil dilation in a testee who is not being deceptive, wherein each of the second-type words is not expected to evoke significant pupil dilation in the testee, wherein the initial word is presented to the testee prior to the presenting of the first-type word and the plurality of second-type words, wherein the entire set of words is presented to the testee in less than 2 minutes, and wherein the set of words contains less than 20 words;

wherein the controller is further programmed to monitor changes in the testee's pupil size during the presenting of the first-type word and the plurality of second-type words and during any responses to the first-type word and the plurality of second-type words made by the testee;

wherein the controller is further programmed to compare changes in the testee's pupil size in response to the first-type word with changes in the testee's pupil size in response to the second-type words to ascertain whether a pupil-dilation response to the first-type word is larger than a pupil-dilation response to each of the plurality of second-type words; and wherein the controller is further programmed to output an indication of deceptiveness or non-deceptiveness based on the ascertaining of whether the pupil-dilation response to the first-type word is larger than the pupil-dilation response to each of the plurality of second-type words, wherein the first-type word and each of the second-type words are all in the same language, and wherein the first-type word and each of the second-type words all have volumes within 10 dB of each other.

19. The apparatus of claim 18, wherein the controller is further programmed to (a) output an indication of deceptiveness when the controller ascertains that the pupil-dilation response to the first-type word is larger than the pupil-dilation response to each of the plurality of second-type words, and (b) output an indication of non-deceptiveness when the controller ascertains that the pupil-dilation response to the first-type word is not larger than the pupil-dilation response to each of the plurality of second-type words.

20. The apparatus of claim 18, wherein the controller is further programmed to control a level of illumination that arrives at the testee's pupil.

21. The apparatus of claim 18, wherein the set of words further includes a third-type word that is expected to evoke significant pupil dilation in a testee who is not being deceptive, and wherein the controller is further programmed to (a) compare changes in the testee's pupil size in response to the third-type word with changes in the testee's pupil size in response to the first-type word to ascertain whether a pupil-dilation response to the first-type word is larger than a pupil-dilation response to the third-type word, (b) output an indication of deceptiveness when the controller ascertains that the pupil-dilation response to the first-type word is larger than the pupil-dilation response to each of the plurality of second-type words and is also larger than the pupil-dilation response to the third-type word, and (c) output an indication of non-deceptiveness when the controller ascertains that the pupil-dilation response to the third-type word is larger than the pupil-dilation response to the first-type word or when the controller ascertains that the pupil-dilation response to the first-type word is not larger than the pupil-dilation response to each of the plurality of second-type words.

22. The apparatus of claim 18, wherein the first-type word and each of the second-type words are presented in the same voice.

23. The apparatus of claim 22, wherein the first-type word and each of the second-type words have a similar level of complexity and a similar language style.

24. A method of evaluating whether a testee is being deceptive, the method comprising:
presenting an introductory phrase or sentence to the testee;
presenting a set of words to the testee after the introductory phrase or sentence has been presented to the testee, with gaps of at least 2 s interposed between words within the set, wherein the set of words includes an initial word, a first-type word, and a plurality of second-type words, wherein the first-type word is expected to evoke significant pupil dilation in a testee who is being deceptive and not to evoke significant pupil dilation in a testee who is not being deceptive, wherein each of the second-type words is not expected to evoke significant pupil dilation in the testee, wherein the initial word is presented to the testee prior to the presenting of the first-type word and the plurality of second-type words, wherein the entire set of words is presented to the testee in less than 2 minutes, and wherein the set of words contains less than 20 words;
monitoring changes in the testee's pupil size during the presenting of the first-type word and the plurality of second-type words and during any responses to the first-type word and the plurality of second-type words made by the testee;
comparing changes in the testee's pupil size in response to the first-type word with changes in the testee's pupil size in response to the second-type words to ascertain whether a pupil-dilation response to the first-type word is larger than a pupil-dilation response to each of the plurality of second-type words; and
outputting an indication of deceptiveness or non-deceptiveness based on the ascertaining of whether the pupil-dilation response to the first-type word is larger than the pupil-dilation response to each of the plurality of second-type words,
wherein the first-type word and each of the second-type words are all in the same language, and
wherein the first-type word and each of the second-type words all have volumes within 10 dB of each other.

25. The method of claim 24, wherein the outputting comprises (a) outputting an indication of deceptiveness when the comparing reveals that the pupil-dilation response to the first-type word is larger than the pupil-dilation response to each of the plurality of second-type words, and (b) outputting an indication of non-deceptiveness when the comparing reveals that the pupil-dilation response to the first-type word is not larger than the pupil-dilation response to each of the plurality of second-type words.

26. The method of claim 24, further comprising controlling a level of illumination that arrives at the testee's pupil.

27. The method of claim 24, wherein the set of words further includes a third-type word that is expected to evoke significant pupil dilation in a testee who is not being deceptive, and
wherein the method further comprises (a) comparing changes in the testee's pupil size in response to the third-type word with changes in the testee's pupil size in response to the first-type word to ascertain whether a pupil-dilation response to the first-type word is larger than a pupil-dilation response to the third-type word, (b) outputting an indication of deceptiveness when the pupil-dilation response to the first-type word is larger than the pupil-dilation response to each of the plurality of second-type words and is also larger than the pupil-dilation response to the third-type word, and (c) outputting an indication of non-deceptiveness when the pupil-dilation response to the third-type word is larger than the pupil-dilation response to the first-type word or when the pupil-dilation response to the first-type word is not larger than the pupil-dilation response to each of the plurality of second-type words.

28. The method of claim 24, wherein the first-type word and each of the second-type words are presented in the same voice.

29. The method of claim 28, wherein the first-type word and each of the second-type words have a similar level of complexity and a similar language style.

* * * * *